(12) United States Patent
Wismayer et al.

(10) Patent No.: US 12,178,706 B2
(45) Date of Patent: Dec. 31, 2024

(54) PROSTHETIC IMPLANT

(71) Applicant: L-Università ta' Malta, Msida (MT)

(72) Inventors: Pierre Schembri Wismayer, Zabbar (MT); Donald Dalli, Zabbar (MT); Joseph Buhagiar, Hal Qormi (MT); Pierluigi Mollicone, Swieqi (MT)

(73) Assignee: L-Università ta' Malta, Msida (MT)

( * ) Notice: Subject to any disclaimer, the term of this patent is extended or adjusted under 35 U.S.C. 154(b) by 426 days.

(21) Appl. No.: 17/596,730

(22) PCT Filed: Jun. 22, 2020

(86) PCT No.: PCT/EP2020/067366
§ 371 (c)(1),
(2) Date: Dec. 16, 2021

(87) PCT Pub. No.: WO2020/260206
PCT Pub. Date: Dec. 30, 2020

(65) Prior Publication Data
US 2022/0233320 A1 Jul. 28, 2022

(30) Foreign Application Priority Data

Jun. 26, 2019 (GB) .................................... 1909181

(51) Int. Cl.
*A61F 2/34* (2006.01)
*A61F 2/36* (2006.01)
(Continued)

(52) U.S. Cl.
CPC .............. *A61F 2/34* (2013.01); *A61F 2/3607* (2013.01); *A61F 2/3609* (2013.01);
(Continued)

(58) Field of Classification Search
CPC ........ A61F 2002/3448; A61F 2002/345; A61F 2002/30652; A61F 2002/30663;
(Continued)

(56) References Cited

U.S. PATENT DOCUMENTS 4,279,041 A * 7/1981 Buchholz .................. A61F 2/40
403/123
4,770,659 A 9/1988 Kendall
(Continued)

FOREIGN PATENT DOCUMENTS

| CN | 109464225 A | 3/2019 |
|----|-------------|--------|
| EP | 2676635 B1 | 12/2015 |

(Continued)

OTHER PUBLICATIONS

International Search Report mailed Sep. 9, 2020, for priority International Patent Application No. PCT/EP2020/067366.
(Continued)

*Primary Examiner* — Alvin J Stewart
(74) *Attorney, Agent, or Firm* — Renner, Otto, Boisselle & Sklar, LLP

(57) ABSTRACT

A prosthetic implant is disclosed comprising: a first component comprising a first inner surface and a first outer surface, a second component comprising a second outer surface adapted to contact and engage with the first inner surface, the second component further comprising a second inner surface, a third component comprising a third outer surface adapted to contact and engage with the second inner surface, the third component further comprising a third inner surface, and a fourth component comprising a fourth outer surface adapted to contact and engage with the third inner surface; wherein the second component is rotatable relative to the first component about a first axis, the third component
(Continued)

is rotatable relative to the second component about a second axis perpendicular to the first axis, and the fourth component is rotatable relative to the third component about a third axis perpendicular to the first axis and second axis; the first inner surface and the second outer surface are each formed with a first partial cylindrical shape, the first inner surface and the second outer surface each comprise a flat surface normal to the first axis and are engageable with one another such that the second component is rotatable relative to the first component about the first axis only, the second inner surface and the third outer surface are each formed with a second partial cylindrical shape, the second inner surface and the third outer surface each comprise a flat surface normal to the second axis and are engageable with one another such that the third component is rotatable relative to the second component about the second axis only, and the third inner surface and the fourth outer surface are each formed with a third partial cylindrical shape, the third inner surface and the fourth outer surface each comprise a flat surface normal to the third axis and are engageable with one another such that the fourth component is rotatable relative to the third component about the third axis only.

24 Claims, 15 Drawing Sheets

(51) Int. Cl.
A61F 2/30 (2006.01)
A61F 2/32 (2006.01)

(52) U.S. Cl.
CPC ............... A61F 2002/30652 (2013.01); A61F 2002/30655 (2013.01); A61F 2002/30663 (2013.01); A61F 2002/3216 (2013.01); A61F 2002/3225 (2013.01); A61F 2002/3448 (2013.01); A61F 2002/3469 (2013.01); A61F 2002/3482 (2013.01); A61F 2002/3654 (2013.01)

(58) Field of Classification Search
CPC ........ A61F 2/34; A61F 2/3607; A61F 2/3609; A61F 2002/30655; A61F 2002/3225; A61F 2002/3216; A61F 2002/3469; A61F 2002/3482; A61F 2002/3454
See application file for complete search history.

(56) References Cited

U.S. PATENT DOCUMENTS

| 7,108,720 | B2 | 9/2006 | Hanes | |
|---|---|---|---|---|
| 7,179,298 | B2 | 2/2007 | Greenlee | |
| 8,858,645 | B2* | 10/2014 | Grostefon | A61F 2/32 623/22.21 |
| 10,111,754 | B2* | 10/2018 | McAlexander | A61F 2/4684 |
| 2002/0116068 | A1 | 8/2002 | McLean | |
| 2003/0171817 | A1* | 9/2003 | Rambert | A61F 2/32 623/22.17 |
| 2004/0193282 | A1* | 9/2004 | Hanes | A61F 2/32 623/22.21 |
| 2011/0251696 | A1* | 10/2011 | Cartillier | A61F 2/32 623/22.21 |
| 2011/0257757 | A1* | 10/2011 | Popoola | A61F 2/32 623/22.15 |
| 2013/0261761 | A1* | 10/2013 | Whitaker | A61F 2/3609 623/22.16 |
| 2013/0345822 | A1* | 12/2013 | Grostefon | A61F 2/36 623/22.18 |
| 2015/0250596 | A1* | 9/2015 | Whitaker | A61F 2/32 623/22.18 |
| 2017/0304061 | A1* | 10/2017 | Grostefon | A61F 2/32 |
| 2018/0092745 | A1* | 4/2018 | McAlexander | A61F 2/3609 |
| 2020/0276022 | A1* | 9/2020 | Sbaiz | A61F 2/30734 |
| 2021/0361440 | A1* | 11/2021 | Wang | A61F 2/30771 |

FOREIGN PATENT DOCUMENTS

| EP | 2830538 B1 | 12/2017 |
|---|---|---|
| WO | 2013148434 A1 | 10/2013 |

OTHER PUBLICATIONS

Written Opinion mailed Sep. 9, 2020, for priority International Patent Application No. PCT/EP2020/067366.
Combined Search and Examination Report issued Dec. 12, 2019, for priority UK Patent Application No. 1909181.8.

* cited by examiner

PROSTHETIC IMPLANT

This application is a national phase of International Patent Application No. PCT/EP2020/067366 filed Jun. 22, 2020, which claims priority to United Kingdom Patent Application No. 1909181.8 filed Jun. 26, 2019, the entire disclosures of which are hereby incorporated by reference.

This invention relates to a prosthetic implant, and particularly, but not exclusively, to a prosthetic implant for use in replacing the hip joint of a patient. The invention is particularly directed to a prosthetic implant for hip replacement of a patient, a method of assembling the prosthetic implant and a method of fitting the prosthetic implant.

The natural anatomy of the hip is based around a ball-and-socket joint, where the 'ball' is the femoral head of the femur or thighbone and the 'socket' is the acetabulum of the pelvis. The ball is able to rotate within the socket with three degrees of freedom. A first degree of freedom represents antero-posterior movement (flexion/extension) of the femur relative to pelvis which primarily occurs when the leg swings backwards and forwards such as when walking, running or kicking a ball. A second degree of freedom represents rotation (medial/lateral rotation) of the femur relative to the pelvis which primarily occurs when twisting the orientation of the leg relative to the torso such as when rotating the body with a foot planted on the ground or moving into a cross-legged sitting position. A third degree of freedom represents lateral movement (abduction/adduction) of the femur relative to the pelvis which primarily occurs when swinging the leg sideways such as when sticking out a leg to balance or side-stepping an obstacle.

The surfaces of the femoral head and the acetabulum are covered with a tissue, called articular cartilage, that cushions the bones. There is also a thin tissue, called a synovial membrane, which surrounds the hip joint and makes a small amount of fluid that lubricates the cartilage to minimise friction. The main ligaments surrounding the hip, located at the intertrochanteric line and ridge, and extending to the edge of the acetabulum, provide stability for the hip joint.

There are various causes of damage to the hip joint that can cause severe pain to a patient, osteoarthritis being the most common. Other causes include but are not limited to, rheumatoid arthritis, post-traumatic arthritis, avascular necrosis and childhood hip disease.

Osteoarthritis occurs when the articular cartilage becomes damaged through wear. Often the wear experienced is greatest at the most superior point (in the direction of the patient's head) of the hip joint where most loads are transferred from the acetabulum to the femoral head.

From here on, all uses of the terms 'superior' and 'inferior' refer to a relative position in the human body, in the direction of the head.

When treatments, such as physio-therapy and pain killers, are no longer effective to treat conditions that cause hip pain to a patient, such as osteoarthritis, a total hip replacement might be required. Also called total hip arthroplasty, the replacement involves removing damaged bone and cartilage and replacing it with prosthetic components.

Known hip prosthetics for total hip replacements may include two key components: an acetabular component and a femoral head component.

Known acetabular components are configured to replicate the function and general shape of an acetabulum socket and may be affixed to the acetabulum of the patient by any suitable means, including bone cement, screws and/or bone growth-inducing material. Known acetabular components may also comprise a liner which might be a different material to the rest of the component, such as ultra-high-molecular-weight polyethylene (UHMWPE) or crosslinked polyethylene (XPE).

Known femoral head components are similarly configured to replicate the function and general shape of the natural femoral head. Extending from known femoral head components is a femoral stem which is configured to engage with the femur shaft of the patient. Some known femoral head and stem components are integrally formed (as a monobloc) from a single material such as stainless steel or cobalt chromium alloy. Other known femoral head and stem components are formed separately, are adapted to engage with one another and may either be formed from the same or different materials. In the latter cases the femoral head may be formed of a ceramic material such as alumina or a metal such as stainless steel or cobalt chromium alloy.

Known hip prosthetics therefore replicate the natural anatomy of the hip joint in that they form a ball-and-socket joint which provides the same three degrees of freedom as the natural hip joint. As prosthetic hips lack the regenerative capabilities of articular cartilage and synovial membrane of the natural hip joint, their lifespan is significantly shorter due to their inability to recover from the detrimental effects of wear.

A common type of hip prosthetic is the 'metal-on-polymer' implant, which comprise a metal femoral head component and a polymer acetabular component. Metal-on-polymer implants particularly suffer from a significant amount of wear, which results in late aseptic loosening, and thus need to be replaced every few years.

Another type of implant is the 'ceramic-on-polymer', which comprises a ceramic femoral head component and a polymer acetabular component. Ceramic-on-polymer implants benefit from greater wear resistance than metal-on-polymer implants due to the ceramic component being more hydrophilic than the metal component and thus generating less friction and wear. Nonetheless, these are also susceptible to aseptic loosening.

Another common type of hip prosthetic is the ceramic implant, where both of the key components are formed of ceramic materials. Although these do not wear, they are very expensive, are prone to squeaking and are vulnerable to fracturing.

A less popular type of hip prosthetic is the 'metal-on-metal' implant. The reason these are less common for modern hip replacement surgeries is the concern over the toxicity of particles generated as the components wear.

A novel hip prosthetic that uses any combination of the less expensive metal and/or polymer materials while having wear characteristics comparable to ceramic implants and still maintaining the three degrees of freedom provided by the natural hip joint would revolutionise the field.

According to a first aspect of the invention there is provided a prosthetic implant comprising: a first component comprising a first inner surface and a first outer surface, a second component comprising a second outer surface adapted to contact and engage with the first inner surface, the second component further comprising a second inner surface, a third component comprising a third outer surface adapted to contact and engage with the second inner surface, the third component further comprising a third inner surface, and a fourth component comprising a fourth outer surface adapted to contact and engage with the third inner surface; wherein the second component is rotatable relative to the first component about a first axis, the third component is rotatable relative to the second component about a second axis perpendicular to the first axis, and the fourth component is rotatable relative to the third component about a third axis perpendicular to the first axis and second axis;

the first inner surface and the second outer surface are each formed with a first partial cylindrical shape, the first inner surface and the second outer surface each comprise a flat surface normal to the first axis and are engageable with one another such that the second component is rotatable relative to the first component about the first axis only, the second inner surface and the third outer surface are each formed with a second partial cylindrical shape, the second inner surface and the third outer surface each comprise a flat surface normal to the second axis and are engageable with one another such that the third component is rotatable relative to the second component about the second axis only, and the third inner surface and the fourth outer surface are each formed with a third partial cylindrical shape, the third inner surface and the fourth outer surface each comprise a flat surface normal to the third axis and are engageable with one another such that the fourth component is rotatable relative to the third component about the third axis only.

In use, in embodiments of the invention, the first outer surface of the prosthetic implant may be affixed to the acetabulum of a patient's pelvis and the fourth component may be rigidly coupled, via a stem section, to the patient's femur, such that the prosthetic implant is usable as a hip prosthetic implant.

In other embodiments of the invention, the configuration of the components may be reversed wherein the first outer surface of the prosthetic implant may be rigidly coupled to the patient's femur and the fourth component may be affixed to the patient's acetabulum, such that the prosthetic implant is usable as a hip prosthetic implant. From here on, when embodiments of the invention are described in use with the first component engaged with an acetabulum and the fourth component engaged with a femur, it will be understood that the configuration may be reversed as stated above.

The ability of the second component to rotate relative to the first component about the first axis, the third component to rotate relative to the second component about the second axis and the fourth component to rotate relative to the third component about the third axis ultimately provides the fourth component with the ability to rotate about three axes relative to the first component. Further, the three axes are perpendicular to one another. Hence, if the first component is engaged with the patient's acetabulum and the fourth component is rigidly coupled, via the stem section, to the patient's femur then the prosthetic implant provides the patient's femur with three degrees of freedom relative to the patient's pelvis, similarly to the natural hip joint.

However, where the natural hip joint and ball-and-socket type prosthetics provide three degrees of freedom with tri-axial rotation between a single pair of contacting surfaces (of the ball and the socket), embodiments of the invention provide three degrees of freedom by means of uni-axial rotation between each of the three pairs of contacting surfaces associated with the four components, consisting of a partial cylindrical design which effectively produces larger contacting areas. Therefore, the same load is applied to articulations with larger surface areas, effectively resulting in three pairs of surfaces that each exhibit lower contact pressure values than those experienced in a ball-and-socket joint articulation, thus effectively reducing the amount of wear that is generated.

From here on, the first, second and third inner surfaces and the second, third and fourth outer surfaces may each be referred to as an "articulating surface", and collectively as the "articulating surfaces". The shared purpose of each of these surfaces is to provide regions of contact where the four components rotate against one another and thereby allow the prosthetic implant to articulate. In this instance, 'allowed to articulate' means that the prosthetic implant is movable without requiring any means of connection or additional component that might be vulnerable to wear or failure.

Further, each articulating surface may be defined as being "continuous", meaning that the surface is free from any abrupt geometrical changes. Adjoining portions of a continuous surface may therefore be considered as being tangential to each other or sharing smooth, flowing geometrical transitions between each other.

Although articulating surfaces of components forming part of the invention are generally smooth (non-rough), definition of surfaces according to embodiments of the invention as being continuous is not intended to define the roughness of those surfaces.

Accordingly, in embodiments of the invention the first, second and third inner surfaces and the second, third and fourth outer surfaces (i.e. the articulating surfaces) are each continuous.

Therefore, in such embodiments of the invention each articulating surface may be free from protrusions, grooves, edges, corners or any other abrupt geometrical changes which may act as sources of wear debris due to the concentration of localized contact stresses.

Therefore the continuous surfaces may further improve the wear resistance of the prosthetic implant.

In embodiments of the invention one or more of the first, second and third partially cylindrical shapes comprises a flat surface and a unilaterally curved surface. Optionally, one or more of the first, second and third partially cylindrical shapes may further comprise a truncated conical surface.

The flat surface forming part of a partially cylindrical shape may correspond to each flat surface forming part of the associated articulating surfaces. For example, the first partially cylindrical shape may comprise a flat surface that corresponds to the flat surfaces forming part of first inner surface and the second outer surface respectively and that are normal to the first axis.

In such embodiments of the invention the unilaterally curved surface and the flat surface may replicate the shape of the natural ankle joint and accordingly constrain motion along a single direction.

The natural ankle joint is significantly more resistant to issues such as osteoarthritis than the hip joint despite carrying a greater load than the hip joint. One hypothesis for this is that the ankle joint's differing structure to the hip joint makes it more resistant to wear. If the hip joint is considered as a 'ball-and-socket' joint, the ankle is a 'hinge' joint and mainly exhibits curvature in one plane only, similarly to a cylinder. This allows primary revolution of the ankle joint about a single axis perpendicular to the leg. The uniplanar curvature of the ankle joint results in the contact area being increased in comparison to a similarly sized ball-and-socket joint, thus the contact stress is reduced.

By replacing the ball-and-socket structure of the hip joint with a composition of three single-axis cylindrically shaped hinge joints, which are each based on ankle joint biomimetics, the overall susceptibility to wear is reduced.

In embodiments of the invention, each articulating surface may comprise a load-bearing surface, or a non-load-bearing surface or both. The load-bearing surfaces are regions of the articulating surfaces that, in use, either transmit a load to another component or receive a load from another component. The non-load-bearing surfaces are surfaces that, in use, do not transmit a load to, or receive a load from, another component.

In such embodiments, the load transmitted through the prosthetic implant is spread across the load-bearing surfaces rather than being focused on a single superior point of a ball-and-socket joint, as is the case in known prosthetic implants. Hence the contact stress and resultant wear is significantly reduced in embodiments of the invention when compared to known prosthetics.

Further, in some embodiments of the invention, the prosthetic implant may be configured to be preferably engageable with the acetabulum and femur of an individual with a larger physique. The size of the components may therefore be increased which in turn increases the size of the load bearing surfaces and reduces the contact pressures experienced. This may be particularly beneficial as an individual with a large physique is likely to impart larger loads through the prosthetic implant.

In embodiments of the invention, the friction experienced at each of the load-bearing surfaces is associated with one of the three degrees of freedom only, so each surface experiences a fraction of the overall friction caused by movement of the joint. Hence the wear exhibited by any single component is further reduced which in turn lengthens the overall life expectancy of the joint before requiring replacement.

In embodiments of the invention at least one of: the unilaterally curved surface, the flat surface and the optional truncated conical surface (forming part of each of the first, second and third partial cylindrical shapes) is adapted to act as the primary load-bearing surface when the prosthetic implant is in use. The primary load-bearing surface is a surface that is perpendicular to the mean load applied when the prosthetic implant is in use. The primary load bearing surface being at least one of: the unilaterally curved surface, the flat surface and the optional truncated conical surface allows the load to be distributed evenly in at least one direction when the prosthetic implant is in use. Therefore point loading is avoided and contact stresses are reduced which in turn reduces the likelihood of wear occurring and wear debris being produced.

In embodiments of the invention, each articulating surface may be formed as a combination of geometric shapes. The geometric shapes may comprise, in part or in full, a cylinder, a planar circle, a truncated cone, a rounded corner, any other suitable geometric shape or any combination thereof. Further, both the load-bearing surfaces and the non-load-bearing surfaces may be formed as one, or any combination of geometric shapes.

In embodiments of the invention, one or more of the components may be formed of any biomaterial suitable for load-bearing joint prostheses, such as stainless steel, cobalt chromium alloy, alumina, and others. In such embodiments, one or more of the components may be formed of ultra-high-molecular-weight polyethylene (UHMWPE) or cross-linked polyethylene (XPE).

UHMWPE is known to exhibit enhanced wear resistance when subjected to uni-directional motion as opposed to multi-directional motion. This characteristic of UHMWPE is due to its unique molecular structure, wherein lamellar crystals orient preferentially to the direction of a sliding motion. If the sliding motion results in a strain large enough to induce plastic deformation, the lamellar crystals are disrupted in such a way to form a fibre-like structure. This leads to orientation hardening, reduced frictional effects, and improved wear resistance in the direction of the sliding motion. The failure strength along the molecular orientation is significantly greater due to carbon bonds. However, this compromises the failure strength in its perpendicular orientation which is only held by weak van der Waals bonds. As the transverse strength is lower than the longitudinal strength, failure is more likely to occur at the inter-fibre section. Nonetheless, transverse stress becomes absent under uni-directional sliding conditions.

In other words, a sliding motion in a first direction against the surface of UHMWPE causes the molecular structure of the UHMWPE to alter in such a way that it becomes more resistant to wear from a sliding motion in the first direction, however it become less resistant to wear in a second direction which is perpendicular to the first direction.

In embodiments of the invention, bearing surfaces formed of UHMWPE are exposed to sliding motions in a single direction only. Therefore, the molecular structure can become preferentially aligned with the direction of motion such that the enhanced wear-resistance characteristics, caused by orientation hardening, are exhibited. The articulating surfaces are never exposed to motion perpendicular to the strong molecular structures in the material and accordingly molecular orientation softening is not exhibited. Hence, not only is the wear reduced because load is spread over large contact areas which reduce the contact stresses, but wear is also reduced because the inherent wear-resistant properties of UHMWPE are harnessed by the design.

In contrast, the ball-and-socket joint surfaces of known metal-on-polymer hip prosthetics, with polymer components formed of UHMWPE, are exposed to sliding motions in multiple directions. Therefore, the sliding motions may regularly be in a direction which is not parallel to the longitudinal axes of the UHMWPE molecular fibres and in which the wear resistance of UHMWPE is weak. Also, sliding motions in such directions will result in molecular orientation softening of UHMWPE, due to the material characteristics described above, which will accelerate wear further. Hence, the multi-directional motion of known hip prosthetics makes them prone to significant and accelerated wear of UHMWPE, which is one reason they need to be replaced as frequently as they do.

Embodiments of the invention may benefit from the use of UHMWPE due to its molecules undergoing orientation hardening when subjected to sliding motions in a single direction. Therefore, embodiments of the invention may have one or more components formed of non-crosslinked UHMWPE wherein molecular orientation hardening is promoted and the preferential material characteristics are harnessed without suffering weakness to motion in multiple directions.

A known method of counteracting the accelerated wear of UHMWPE ball-and-socket implants is to crosslink the molecular fibres, producing XPE. This involves modifying the molecular structure of UHMWPE so that carbon bonds form between the various linear carbon chains that are present. Carbon bonds are much stronger than van der Waals bonds which retards the chain mobility. This results in the polymer possessing an increase in ultimate strength and a decrease in ductility. Furthermore, the wear resistance is enhanced since the extent of molecular rearrangement is limited in all directions. However, XPE is prone to oxidation effects due to the generation of free radicals, leading to embrittlement and a reduction in the fatigue strength. To counteract this problem, antioxidants such as vitamin E are included to limit the mobility of the free radicals. Despite the increased number of crosslinks, XPE is still susceptible to molecular reorientation, however at lower extents.

In embodiments of the invention, one or more components may be formed of XPE to exploit the inherent lower wear benefits of the design, due to the large contacting areas and the uni-directional sliding motion of the components and its molecular reorientation mechanisms. The large contact areas result in reduced contact stresses which consequently maintain the fatigue strength of the components. Although crosslinking limits the molecular reorientation of the polymer chains in XPE, the uni-directional motion of the components generates sufficient orientation hardening effects to produce significant reductions in wear. Therefore, the molecular structure of XPE would still become preferentially aligned with the direction of motion, thus benefiting from the newly formed structure with enhanced wear resistance. Both the rate and proportion of orientation hardening in XPE are lower than those exhibited in UHMWPE.

In embodiments of the invention, the prosthetic implant, in use, may be assembled such that the fourth component is engaged with the third component, which is in turn engaged with the second component, which is in turn engaged with the first component, all without requiring any means of attaching, joining or securing one component to another. In particular, engagement of the third component with second component and engagement of the second component with the first component may result in those components becoming rotatably interlocked with one another due to complimentary geometry of those components.

In known prosthetics of this type, joint features such as notches and protrusions between components are typically relatively vulnerable to failure. Alternatively, known prosthetics of this type may comprise additional components such as linkages or bearings which provide additional sources for wear and potential failure.

In embodiments of the invention, there is no need to have notches, protrusions or additional components to permit the core components to attach or connect together. In such embodiments of the invention, all surfaces of all components may therefore be continuous. As a result a prosthetic implant according to such embodiments of the invention will be more robust against failure when compared to known prosthetic implants because it doesn't comprise features such as notches and protrusions or additional components such as linkages or bearings which are particularly vulnerable to wear or failure or both.

In embodiments of the invention, the partial cylindrical shape comprises a rounded corner.

In such embodiments, all articulating surfaces of all components may be continuous. Each of the components may therefore be particularly wear resistant as there are no apexes nor are there sharp edges or corners at which wear could be focused. The rounded corners may also form part of the load-bearing surfaces and thereby increase the area over which the load is spread when the prosthetic implant is in use. Hence the contact stress and resulting wear is reduced.

In embodiments of the invention, the first inner surface forms a first recess comprising a first opening; the first component further comprises a first lip adapted to define part of the opening and shaped such that the area of the first opening is smaller than the maximal cross-sectional area of the first recess; and the second component is engageable with the first component, and particularly with the first lip, such that the second component is held within the first recess.

In such embodiments, the second component may be passed through the first opening in a certain orientation to fit within the first recess and then be rotated such that it can no longer pass through the first opening or dislocate from the first recess. In some embodiments the degree of rotation of the second component may be 180° about the first axis from the position it has when the prosthetic implant is fully assembled. If the third and fourth components are engaged with the second component it may then be impossible for the second component to rotate to an orientation in which it can again fit through the first opening. Hence the second component is interlocked within the first component whilst at the same time being free to rotate about the first axis in the range of motion used by the patient. Therefore the risk of the second component dislocating from the first component (out of the first recess) is greatly reduced.

In embodiments of the invention, the second inner surface forms a second recess comprising a second opening; the second component further comprises a second lip adapted to define part of the opening and shaped such that the area of the second opening is smaller than the maximal cross-sectional area of the second recess; and the third component is engageable with the second component, and particularly with the second lip, such that the third component is held within the second recess.

In such embodiments, the third component may be passed through the second opening in a certain orientation to fit within the second recess and then rotated such that it can no longer pass through the second opening or dislocate from the second recess. In some embodiments the degree of rotation of the third component may be 180° about the second axis from the position it has when the prosthetic implant is fully assembled. If the fourth component is engaged with the third component it may then be impossible for the third component to rotate to an orientation in which it can again fit through the second opening. Hence the third component is interlocked within the second component whilst at the same time being free to rotate about the first and second axes in the range of motion used by the patient. Therefore the risk of the third component dislocating from the second component (out of the second recess) is greatly reduced.

In such embodiments the only components of the prosthetic implant which don't interlock may be the third and fourth components. This means that the risk of dislocation is, at most, equal to known ball-and-socket type prosthetics. Other known prosthetics may be prone to a greater chance of dislocation due to the absence of interlocking features or the inclusion of connection features which may fail and lead to dislocation.

In embodiments of the invention, the first outer surface is adapted such that, in use, it is engageable with an acetabulum.

In such embodiments, the first outer surface may be shaped and/or sized to the extent that, in use, it may preferentially engage with the acetabulum of the patient. The first outer surface may also be adapted to the extent that, in use, it may interact with a means of affixing the first component to the acetabulum of the patient such as securing the first component inside a shell to be fixed to the acetabulum using screws, using bone cement, using bone growth-inducing material or using any combination thereof. Any adaption of the first outer surface to the extent that, in use, it may readily engage with the acetabulum of a patient will reduce the likelihood of the prosthetic implant coming loose or failing, which would require surgery to rectify either by repair or replacement.

In such embodiments, the first component may be asymmetrically shaped to preferentially engage with either the left or the right acetabulum of a patient. The asymmetry of the first component may be the result of an extended wall of the first component so that, when the first component is engaged with either the left or the right acetabulum of the patient, the extended wall is positioned as an extended posterior wall that allows a greater range of movement of the hip with reduced risk of dislocation.

In such embodiments, the second component may also be asymmetrically shaped to preferentially engage with the asymmetrical first component described above. Further, in such embodiments, the second component may comprise a reduced anterior wall. The asymmetry of the second component may be advantageous in allowing a patient to perform activities of daily living that require extreme joint angles, such as squatting, whilst at the same time retaining a high level of stability without the risk of dislocation or impingement.

In embodiments of the invention, the first outer surface further comprises an engagement feature adapted such that, in use, the first component is engageable with an acetabulum.

In such embodiments, the engagement feature may comprise concentric and/or radial features which, in use, permit the first outer surface to grip the acetabulum of a particular patient to support fixation via bone cement or bone growth-inducing material.

The engagement feature may alternatively be configured to interact with a shell that will, in use, support fixation to the acetabulum via cement, bone screws or bone growth-inducing material. In such embodiments, the prosthetic implant may further comprise a shell component engageable with an acetabulum wherein the first component is configured as a liner adapted to engage with the shell component.

In embodiments of the invention, the fourth component further comprises a stem, which stem is engageable, in use, with a femur.

In such embodiments, the fourth component and stem may be formed of the same material in a single piece, as a monobloc design, that doesn't require any joint that may be vulnerable to wear, fretting and failure. The stem may be shaped and/or sized to the extent that, in use, it may preferentially engage with the femur of a particular patient. The stem may also be adapted to interact with a means of affixing the fourth component, in use, to the femur of the patient such as bone cement, screws and/or bone growth-inducing material. Any adaption of the stem to engage with the femur of a patient will reduce the likelihood of the prosthetic implant coming loose or failing when in use, which would require surgery to rectify either by repair or replacement.

In such embodiments, flat surfaces on a head of the fourth component may be parallel to flat surfaces on the stem of the fourth component. This allows the fourth component to be produced more cost-effectively with a simplified manufacturing process.

Components with a monobloc design, such as the fourth component in such embodiments of the invention, may for example be manufactured via a 3-Axis computer numerical control (CNC) machining process. 3-Axis CNC machining is relatively simple, and is therefore cost effective, and involves a machining tool that has free range of movement in a two-dimensional plane as it must machine from the top down in a direction normal to that plane. Therefore, the majority of costs associated with CNC machining that are due to manual reorientation of the parts to be machined in order to achieve the correct orientation relative to the machining tool are reduced. By comprising as many parallel surfaces as possible, less manual reorientation is require and the machining costs may therefore be reduced.

Known ball-and-socket type prosthetic implants are, in most cases, produced as two separate components due to the difficulty in machining a spherical ball shape in a monobloc design with the associated stem. As the two components are separate, they are vulnerable to fretting whereas the monobloc design of embodiments of the invention are not.

In embodiments of the invention, the prosthetic implant further comprises a fifth component, engageable with the fourth component and comprising a stem, which stem is, in use, engageable with a femur.

In such embodiments, the fourth component and fifth components may be formed separately, in a modular design. The fourth component may be adapted to engage with the fifth component by any suitable means. For example the fourth and fifth components may be engaged with a mechanical key. Alternatively, the fifth component may comprise a square shaft (or other cross-sectional shapes) that fits within a complimentarily shaped recess in the fourth component, thereby guaranteeing alignment of the fourth and fifth components when engaged.

In embodiments of the invention, the fifth component further comprises a tapered protrusion with at least one flat outer surface and the fourth component further comprises a fourth recess that is tapered with at least one flat inner surface and configured complementarily to the tapered protrusion of the fifth component.

In such embodiments, the tapered protrusion may fit within the fourth recess and the at least one flat outer surface may abut against the at least one flat inner surface. Abutting the at least one flat outer surface against the at least one flat inner surface may permit alignment of the fifth component with the fourth component and may stop the fifth component from rotating relative to the fourth component.

In other embodiments of the invention, the tapered protrusion and corresponding fourth recess may be adapted to have a round taper without a flat surface. In such embodiments, an external instrument would be required to correctly align the fifth component with the fourth component.

In embodiments of the invention, in use, the first axis aligns with a flexion and extension axis defined by a natural hip joint.

In such embodiments, the alignment of the first axis with the anatomical axis about which flexion and extension occurs, allows movements of flexion or extension to be performed with minimal overall movement of the components relative to one another. This is due to minimal rotation of the components about the other two axes. Reducing the overall movement that occurs in flexion and extension of the leg in turn reduces the total sliding motions of the components against one another and hence reduces the overall wear experienced.

Further, the alignment of the first axis with the flexion and extension axis of the natural hip joint means that, in use, loads on the prosthetic implant are efficiently transferred from the first inner surface to the second outer surface because the load is normal to substantial regions of the surfaces, which results in reduced contact pressure. The loads placed on the prosthetic implant, in use, comprise a combination of body weight, muscle forces and forces of inertia from movement of the body.

In embodiments of the invention, first inner load-bearing surface and second outer load-bearing surface are larger than the other load-bearing surfaces provided by the prosthetic implant according to embodiments of the invention. This means that the load transmitted from the first component to the second component is spread over a larger area than the loads transmitted from the second component to the third component and from the third component to the fourth component. In other embodiments of the invention, the first and second components may not be the largest components. In further embodiments the components that provide flexion and extension of the hip joint may not be the largest components.

The major movements of the leg require revolution about the 'flexion/extension' axis. In embodiments of the invention the first axis is aligned with the anatomical degree of freedom that provides flexion and extension of the leg, hence the loads associated with this movement are spread across the largest load-bearing surfaces available. This minimises the contact pressure exerted by the most common form of load transmitted through the prosthetic implant according to embodiments of the invention. The result is that the amount of wear is reduced in the direction that is usually associated with the highest risk of wear.

In other embodiments of the invention, the first axis may be defined to provide medial and lateral rotation or abduction and adduction of a leg relative to a pelvis. Therefore, the first axis may be adapted to align with any one of the three anatomical degrees of freedom provided by a natural hip joint.

In embodiments of the invention, in use, the second axis aligns with a medial and lateral rotation axis defined by a natural hip joint.

In such embodiments, the alignment of the second axis with the anatomical axis about which medial and lateral rotation occurs allows movements of medial or lateral rotation to be performed by embodiments of the invention in use with minimal overall movement of the components relative to one another. This is due to minimal rotation of the components about the other two axes. Reducing the overall movement that occurs in rotation of the leg in turn reduces the total sliding motions of the components against one another and hence reduces the overall wear experienced.

Further, the alignment of the second axis with the medial/lateral rotation axis of the natural hip joint means that, in use, loads on the prosthetic implant are efficiently transferred from the second inner surface to the third outer surface because the load is mostly normal to substantial regions of the surfaces, which results in reduced contact pressure. In such embodiments of the invention, the substantial regions of the surfaces that experience normal loading may be shaped as a planar circular portion of the surfaces.

In other embodiments of the invention, the second axis may be defined to provide flexion and extension or abduction and adduction of a leg relative to a pelvis. Therefore, the second axis may be adapted to align with any one of the three anatomical degrees of freedom provided by a natural hip joint.

In embodiments of the invention, in use, the third axis aligns with an abduction/adduction axis defined by a natural hip joint.

In such embodiments, the alignment of the third axis with the anatomical axis about which abduction and adduction occurs, allows movements of abduction or adduction to be performed by embodiments of the invention in use with minimal overall movement of the components relative to one another. This is due to minimal rotation of the components about the other two axes. Reducing the overall movement that occurs in abduction and adduction of the leg in turn reduces the total sliding motions of the components against one another and hence reduces the overall wear experienced.

Further, the alignment of the third axis with the abduction and adduction rotation axis of the natural hip joint means that, in use, loads on the prosthetic implant are efficiently transferred from the third inner surface to the fourth outer surface because the load is normal to the surfaces, which results in reduced contact pressure.

In other embodiments of the invention, the third axis may be defined to provide flexion and extension or medial and lateral rotation of a leg relative to a pelvis. Therefore, the third axis may be adapted to align with any one of the three anatomical degrees of freedom provided by a natural hip joint.

In embodiments of the invention, the first, second, third and fourth components are formed of alternating polymeric and metallic materials, or alternating polymeric and ceramic materials, or any combination of polymeric, metallic and ceramic materials.

In such embodiments, the polymeric material may be a polyethylene such as UHMWPE, XPE or any other suitable polymer, the metallic material may be stainless steel, cobalt chromium alloy or any other suitable metal alloy and the ceramic material may be alumina ($Al_2O_3$), zirconia ($ZrO_2$) or any suitable technical ceramic material. Alternation of polymeric materials with either metal or ceramic materials allows the strengths of each material to be harnessed. Metals and ceramics exhibit excellent wear resistance when they are exposed to friction against polymeric materials. Meanwhile polymers have a low elastic modulus which enables a better conformal design. Further, if the polymer is UHMWPE or XPE then the directionally enhanced wear resistance discussed above is also exhibited to further improve the overall wear resistance of the prosthetic implant.

In embodiments of the invention, the first, second, third and fourth outer surfaces are partially convex.

In such embodiments, the first outer surface is preferentially shaped, such that in use it may engage with the concave acetabulum of the patient. The second outer surface is then similarly preferentially shaped to engage with the first component to maximise surface area while minimising the use of volumetric space. Similar relationships are then present for the third and fourth outer surfaces relative to the second and third components respectively.

In embodiments of the invention, the first, second and third inner surfaces are partially concave.

In such embodiments, the concave inner surfaces may replicate the shape of both the natural acetabulum and the natural ankle socket which improves the fit of the prosthetic implant in a patient's acetabulum and the wear resistance respectively. Also, as stated above, the first, second, third and fourth outer surfaces may be convex. Therefore, the concave inner surfaces are complimentarily shaped to (a) be formed opposite the convex outer surface of the same component and (b) be able to engage with the associated outer surface of the adjacent component.

According to a second aspect of the invention there is provided a method for assembling a prosthetic implant comprising a first component comprising a first outer surface and a first inner surface, a second component comprising a second outer surface and a second inner surface, a third component comprising a third outer surface and a third inner surface and a fourth component comprising a fourth outer surface and the fourth component is rotatable relative to the third component about a third axis perpendicular to the first axis and second axis; the method comprising the steps: engaging the third component with the second component, rotating the third component relative to the second component, about the second axis, until the third outer surface becomes rotatably interlocked in contact with the second inner surface, engaging the second component with the first component, rotating the second component relative to the first component, about the first axis, until the second outer surface becomes rotatably interlocked with the first inner surface, and engaging the fourth component with the third component.

By means of the second aspect of the invention, a method is provided for assembling a prosthetic implant according to the first aspect of the invention. First, the third component is engaged with the second component and rotated relative to the second component about the second axis such that the third outer surface becomes rotatably interlocked in contact with the second inner surface, thereby mating the two surfaces. Then the second component is engaged with the first component and rotated relative to the first component about the first axis such that the second outer surface becomes rotatably interlocked in contact with the first inner surface, thereby mating the second outer surface and first inner surface similarly to the third outer surface and second inner surface. Finally, the fourth component is engaged with the third component, via the fourth outer surface and the third inner surface rotatably contacting one another, such that each component is now engaged with its adjacent component or components. In use, this step may be performed similarly to the reduction of a natural hip dislocation in which the femoral head is relocated within the acetabulum.

In such embodiments, the rotation of the third component relative to the second component and the rotation of the second component relative to the first component may each be a rotation of approximately 180° about the respective axis. However, it is to be understood that a rotation of more or less than 180° may be carried out and interlocking of the relevant articulating surfaces may still be achieved.

Also, the method is reversible in order to disassemble prosthetic implant as the method avoids any steps of affixing, securing of joining two or more components together. As such, there are no connections which can fail, hence reducing the chance that the prosthetic implant can fail and need replacing.

In other embodiments of the invention, the order of the steps may be changed as follows: engaging the second outer surface with the first inner surface, rotating the second component through 180 degrees relative to the first component, engaging the third outer surface with the second inner surface, rotating the third component through 180 degrees relative to the second component, engaging the fourth outer surface with the third inner surface.

In embodiments of the invention, wherein the first component further comprises a first recess comprising a first opening shaped to have a smaller opening area than the maximal cross-sectional area of the first recess; the method step of: engaging the second component with the first component, comprises the steps of: orienting the second component such that it can pass through the first opening, positioning the second component through the first opening, into the first recess and contacting and engaging the second outer surface with the first inner surface.

In such embodiments, the second component may be sized and shaped such that it can pass through the first opening in certain orientations only. The second component may also be sized and shaped such that once positioned through the first opening, it fills the first recess such that all parts of the second outer surface may contact against corresponding parts of the first inner surface.

In embodiments of the invention, the method step of rotating the second component relative to the first component, comprises the step of: changing the orientation of the second component such that it can no longer pass through the first opening.

In such embodiments, by changing the orientation of the second component from the orientation at which it can pass through the first opening, the second component becomes held within the first recess, restricted by the first opening. Hence, the second component becomes interlocked with the first component and remains engaged without requiring any form of attachment or join. This interlocking of the components vastly reduces the chance of the second component unintentionally dislocating from the first component, yet the method of assembly to be performed by a practitioner is very simple and intuitive as no additional parts or fixing mechanisms are required.

In embodiments of the invention, wherein the second component further comprises a second recess comprising a second opening shaped to have a smaller opening area than the maximal cross-sectional area of the second recess; the method step of: engaging the third component with the second component, comprises the steps of: orienting the third component such that it can pass through the second opening, positioning the third component through the second opening, into the second recess and contacting and engaging the third outer surface with the second inner surface.

In such embodiments, the third component may be sized and shaped such that it can pass through the second opening in certain orientations only. The third component may also be sized and shaped such that once positioned through the second opening, it fills the second recess such that all parts of the third outer surface may contact against corresponding parts of the second inner surface.

In embodiments of the invention, the method step of rotating the second component relative to the first component, comprises the step of: changing the orientation of the second component such that it can no longer pass through the first opening.

In such embodiments, by changing the orientation of the third component from the orientation at which it can pass through the second opening, the third component becomes held within the second recess, restricted by the second opening. Hence, the third component becomes interlocked with the second component and remains engaged without requiring any form of attachment or join. This interlocking of the components vastly reduces the chance of the third component unintentionally dislocating from the second component, yet the method of assembly to be performed by a practitioner is very simple and intuitive as no additional parts or fixing mechanisms are required.

According to a third aspect of the invention there is provided a method of for fitting a prosthetic implant comprising a first component comprising a first outer surface and a first inner surface, a second component comprising a second outer surface and a second inner surface, a third component comprising a third outer surface and a third inner surface and a fourth component comprising a fourth outer surface, wherein the second component is rotatable relative to the first component about a first axis, the third component is rotatable relative to the second component about a second axis perpendicular to the first axis; the method comprising the steps: engaging the third component with the second component, rotating the third component relative to the second component, about the second axis, until the third outer surface becomes rotatably interlocked in contact with the second inner surface, engaging the second component with the first component, rotating the second component relative to the first component, about the first axis, until the second outer surface becomes rotatably interlocked in contact with the first inner surface, fixing the first outer surface with an acetabulum of a patient, fixing the fourth component with a femur of a patient, and engaging the fourth component with the third component.

By means of the third aspect of the invention, a method is provided for fitting a prosthetic implant according to the first aspect of the invention within a patient. The prosthetic implant is partially assembled by first engaging the third component with the second component and rotating the third component relative to the second component about the second axis such that the third outer surface becomes rotatably interlocked in contact with the second inner surface, thereby mating the two surfaces. Then the second component is engaged with the first component and rotated relative to the first component about the first axis such that the second outer surface becomes rotatably interlocked in contact with the first inner surface, thereby mating the second outer surface and first inner surface also.

The first component, with the second and third components interlocked within it, is fixed to the acetabulum of a patient's pelvis. Similarly, the fourth component is fixed to the patient's femur. Finally, the fourth component is engaged with the third component such that each component is now engaged with its adjacent component or components. This step may be performed similarly to the reduction of a natural hip dislocation in which the femoral head is relocated within the acetabulum.

In such embodiments, the rotation of the third component relative to the second component and the rotation of the second component relative to the first component may each be a rotation of approximately 180° about the respective axis. However, it is to be understood that a rotation of more or less than 180° may be carried out and mating of the relevant articulating surfaces may still be achieved.

Also in such embodiments, there are no steps of fitting the prosthetic implant to the patient which would increase the surgical complexity beyond the surgery that would be required to fit known ball-and-socket type prosthetics within a patient. The steps that differentiate the fitting of embodiments of the invention from methods of fitting known ball-and-socket type prosthetics are engaging the third and second outer surfaces with the second and first inner surfaces respectively and rotating the third and second components in order to interlock them with the second and first components respectively. These steps are simple and intuitive for a practitioner to perform and, further, they do not require precision, nor the application of any forces, for example to 'snap', 'screw' or 'wedge' a component into position within the patient. Additionally, the steps of assembling the first, second and third components can be carried out before implantation, therefore further simplifying the implantation method.

A further difference between embodiments of the invention and methods of fitting known ball-and-socket type prosthetics is that the alignment of the first component of the invention must be accurate whereas the acetabular cup components of known prosthetic implants are axisymmetric and therefore do not require accurate alignment. In embodiments of the invention, markers may be provided on the lip of the first component to indicate the superior, inferior, anterior and posterior directions of the component to guide a surgeon to achieve the correct orientation. Overall, the method does not require any additional surgical knowledge for a practitioner to perform, yet once fitted the prosthetic implant may offer all of the advantages to the patient associated with the first aspect of the invention described above.

In some embodiments of the invention the fourth component may be fixed to the femur of the patient before the first component (pre-assembled with the second and third components) is fixed to the acetabulum of the patient. However, due to the simplicity of these steps there would be no increase in the hip replacement surgery's complexity.

In other embodiments of the invention, the order of the steps may be changed as follows: engaging the second outer surface with the first inner surface, rotating the second component through 180 degrees, about the first axis, relative to the first component, engaging the third outer surface with the second inner surface, rotating the third component through 180 degrees, about the second axis, relative to the second component, fixing the first outer surface with an acetabulum of a patient, fixing the fourth component with a femur of a patient, engaging the fourth outer surface with the third inner surface.

The invention will now be described by way of example only with reference to the accompanying drawings in which.

Figure 25:
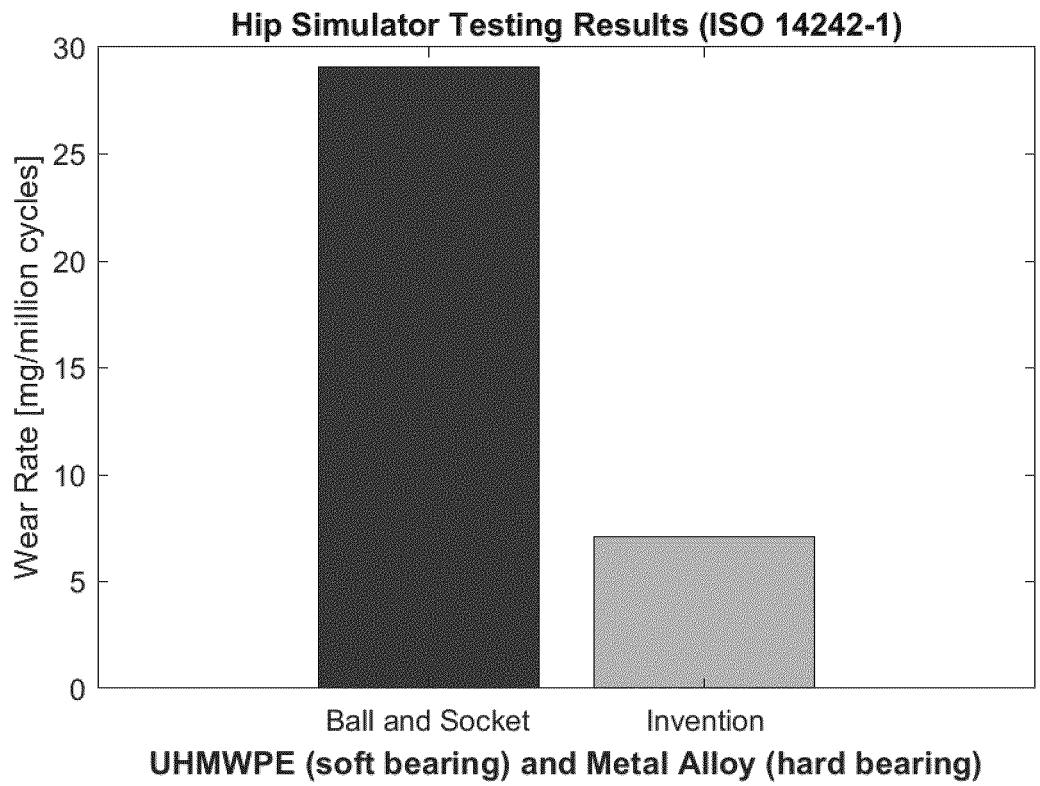

FIG. 25 is a graphical representation comparing the experimental wear rate of a prosthetic implant according to an embodiment of the first aspect of the invention against a known ball-and-socket type prosthetic implant, both of which use UHMWPE as the soft bearing material and a metal alloy as the hard bearing material, according to the standard test to measure the wear of total hip-joint prostheses (ISO 14242-1).

Figure 26:
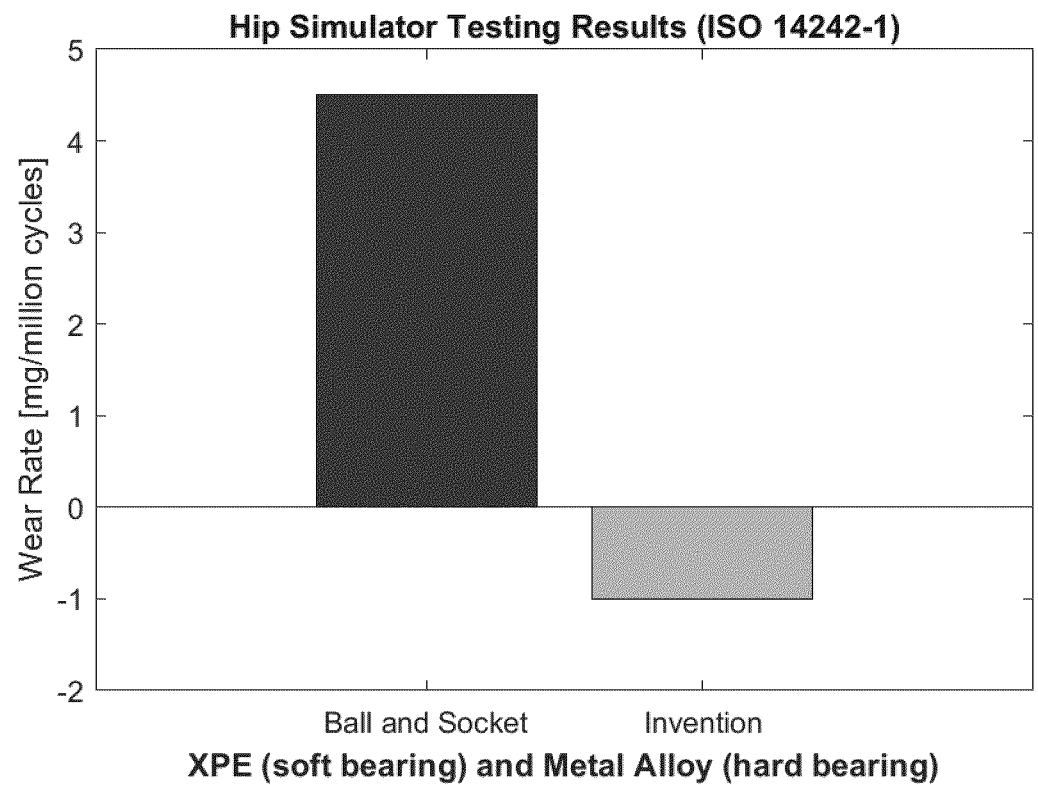

FIG. 26 is a graphical representation comparing the experimental wear rate of a prosthetic implant according to an embodiment of the first aspect of the invention against a known ball-and-socket type prosthetic implant, both of which use XPE as the soft bearing material and metal alloy as the hard bearing material, according to the standard test to measure the wear of total hip-joint prostheses (ISO 14242-1).

Figure 1:
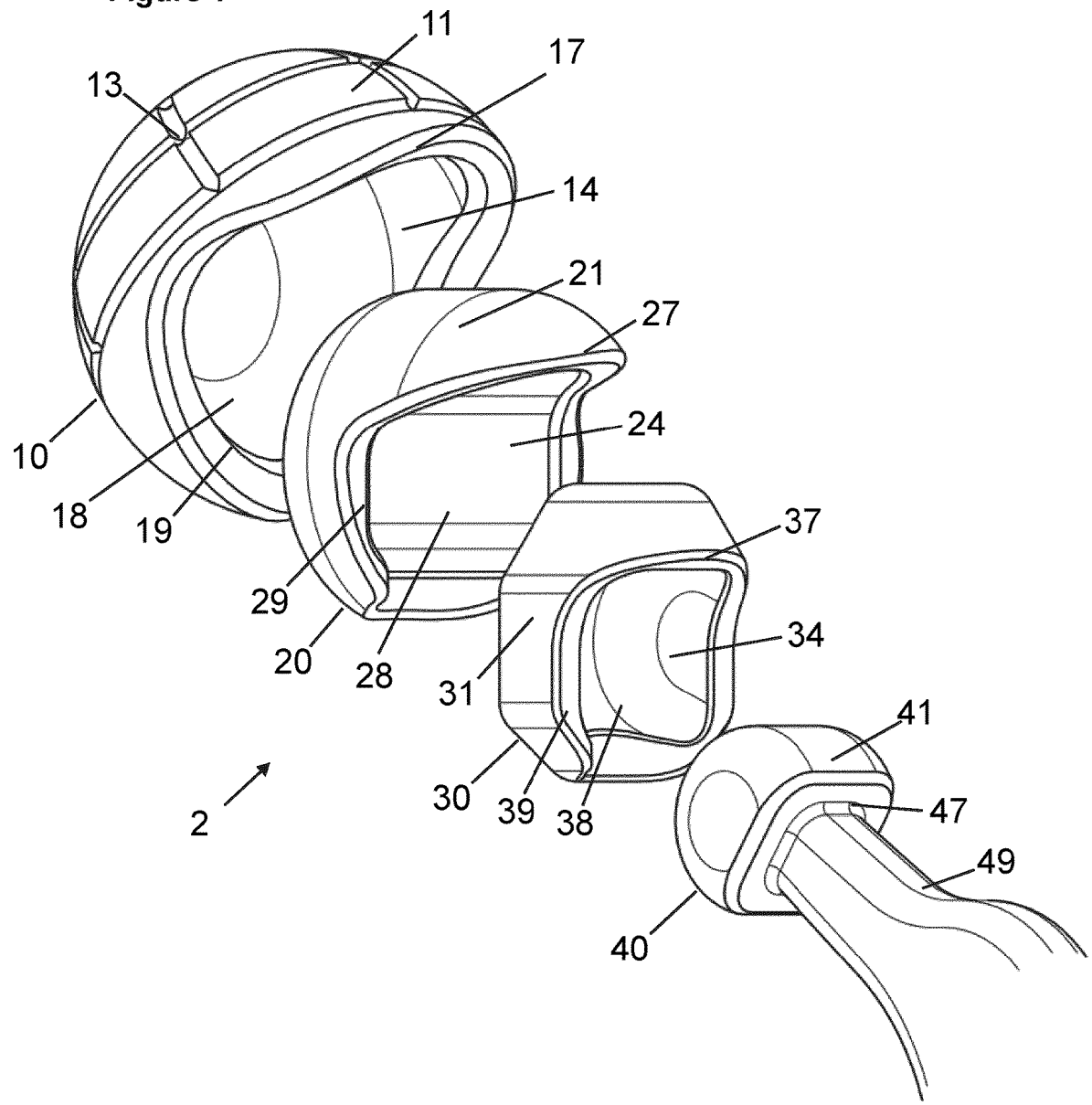
FIG. 1 is an exploded view of a prosthetic implant, according to an embodiment of the first aspect of the present invention, showing first, second, third and fourth components spaced apart from one another.

Referring initially to FIG. 1, a prosthetic implant according to an embodiment of the first aspect of the present invention, is defined generally by the reference numeral 2. The prosthetic implant 2 comprises a first component 10, a second component 20, a third component 30 and a fourth component 40.

The first component 10 comprises a first outer surface 11, a first inner surface 14, a first lip 17 and a first recess 18 comprising a first opening 19. The first outer surface 11 comprises an engagement feature 13 adapted to permit engagement of the first component with the acetabulum of a patient's hip.

The second component 20 comprises a second outer surface 21 adapted to contact and engage with the first inner surface 14 such that the second component 20 is able to rotate against the first component 10. The second component further comprises a second inner surface 24, a second lip 27 and a second recess 28 comprising a second opening 29.

The third component 30 comprises a third outer surface 31 adapted to contact and engage with the second inner surface 24 such that the third component 30 is able to rotate against the second component 20. The third component 30 further comprises a third inner surface 34, a third lip 37 and a third recess 38 comprising a third opening 39.

The fourth component 40 comprises a head 47 and a fourth outer surface 41 formed around the head 47 and adapted to contact and engage with the third inner surface 34 such that the fourth component 40 is able to rotate against the third component 30. The fourth component is coupled to and integrally formed with a stem 49 extending from the head 47 and adapted to engage with the femur of the patient.

Figure 2:
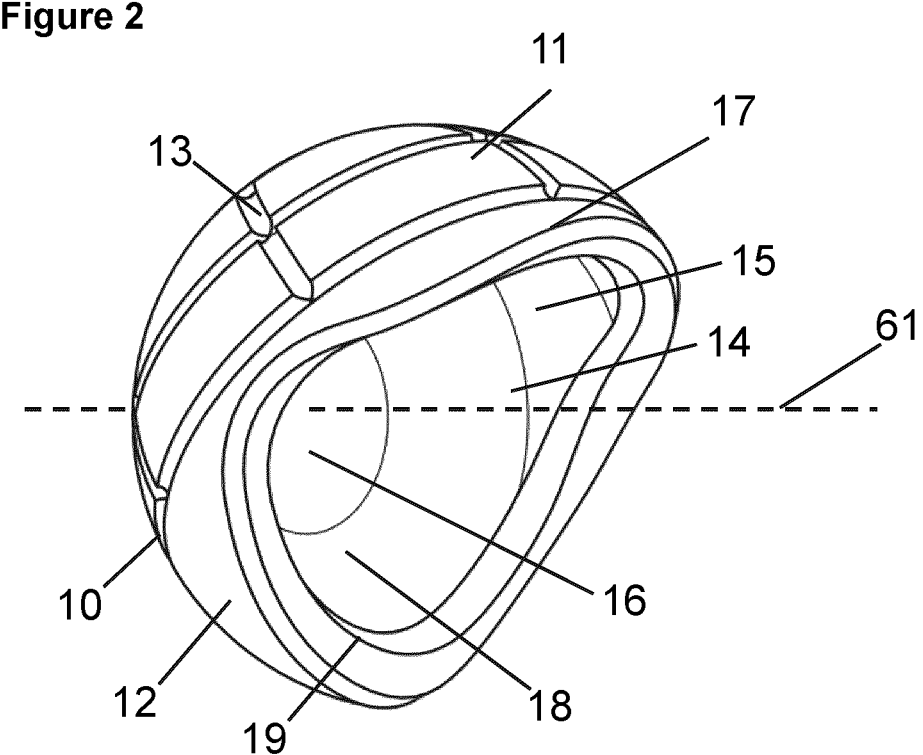
FIG. 2 is an illustration of the first component shown in FIG. 1.

Referring now to FIG. 2, the first component 10 is shown. The first inner surface 14 comprises a first inner load-bearing surface 15 and a first inner non-load-bearing surface 16. The shape of the first inner surface 14 is formed of a partial cylindrical surface with rounded edges and comprising a flat circular surface. The partial cylindrical surface and adjacent rounded edges act as the first inner load-bearing surface 15. The flat circular surface acts as the first inner non-load-bearing surface 16.

Also shown relative to the first component 10 is a first axis 61.

When in use, the embodiment of the first component 10 shown in FIG. 2 is engaged with the right acetabulum of a patient, the right-hand side of the first opening 19 corresponds to the anterior (front) side of the acetabulum. The left-hand side of the first opening 19 therefore corresponds to the anterior (rear) side of the acetabulum.

The embodiment of the invention, and specifically of the first component 10, shown in FIG. 2 is adapted to be preferably engageable with the right acetabulum of a patient. The first opening 19 is asymmetrical in shape wherein the first component comprises an extended wall 12 so that the posterior side extends further than the anterior side. The extended wall 12 provides the patient with a greater range of movement in their prosthetic hip joint with a reduced risk of dislocation. In particular, the patient will be able to achieve high flexion angles (when raising their leg forward) with reduced risk of dislocation of the second component from the first component.

In an alternate embodiment, the configuration of the first component 10 shown in FIG. 2 may be mirrored in order to provide a first component 10 adapted to preferentially engage with the left acetabulum of a patient.

In other embodiments of the invention, the first component 10 may adapted to engage with either a left acetabulum or a right acetabulum of a patient wherein the first opening 19 is symmetrical in shape.

Figure 3:
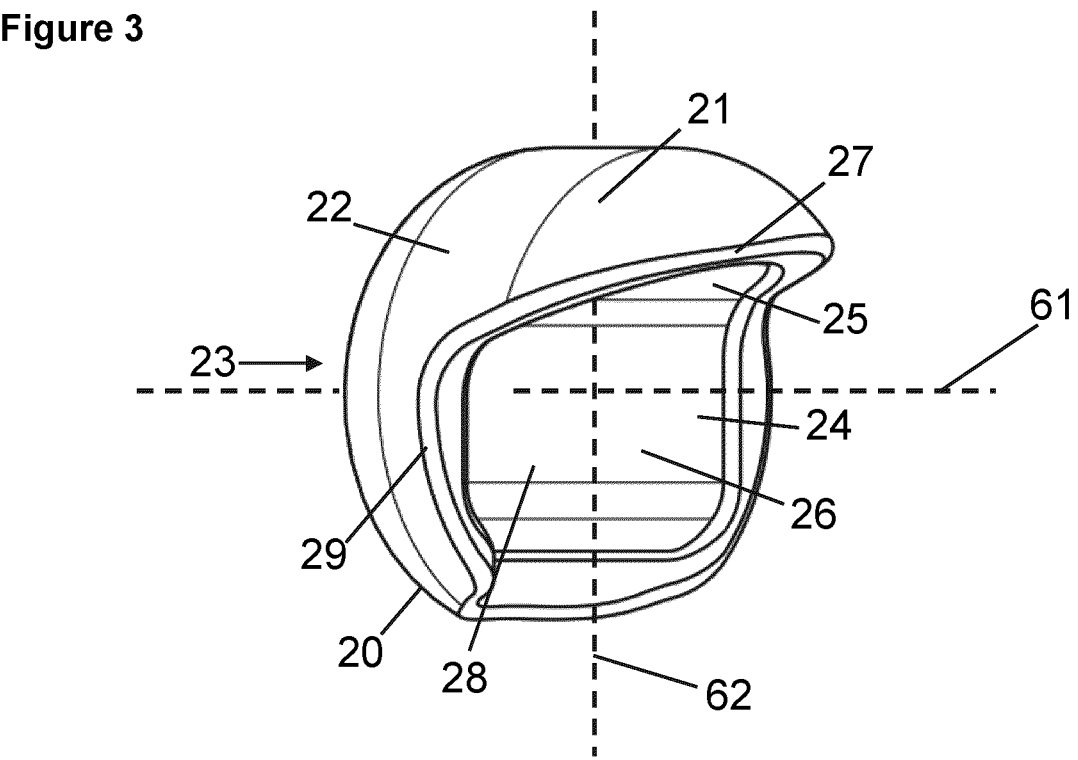
FIG. 3 is an illustration of the second component shown in FIG. 1.

Referring now to FIG. 3, the second component 20 is shown. The second outer surface 21 is adapted to have a geometry that compliments the first inner surface 14 and comprises a second outer load-bearing surface 22 and a second outer non-load-bearing surface 23 which correspond with the first inner load-bearing surface 15 and the first inner non-load-bearing surface 16 respectively.

The second inner surface 24 comprises a second inner load-bearing surface 25 and a second inner non-load-bearing surface 26. The shape of the second inner surface 24 is formed of a partial cylindrical surface, two opposed truncated cone surfaces and a flat circular surface, each with rounded edges. The flat circular surface, the superior truncated cone surface and the associated rounded edges act as the second inner load-bearing surface 25. The partial cylindrical surface and the inferior truncated surface act as the second inner non-load-bearing surface 26.

Also shown relative to the second component 20 is the first axis 61 and a second axis 62 which is perpendicular to the first axis 61.

The first inner surface 14 and the second outer surface 21 are configured such that, when engaged with one another, the second component 20 is rotatable relative to the first component 10 about the first axis 61 only. In use, the first axis 61 aligns with an anatomical degree of freedom and provides flexion and extension of a leg relative to a pelvis. Hence, the first axis 61 may be considered as the flexion-extension axis in this embodiment of the invention.

Figure 4:
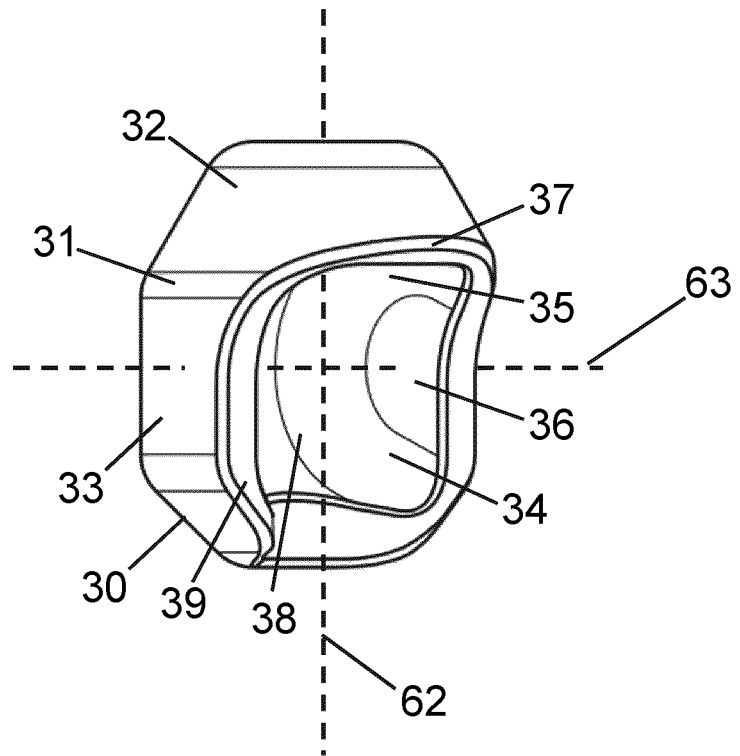
FIG. 4 is an illustration of the third component shown in FIG. 1.

Referring now to FIG. 4, the third component 30 is shown. The third outer surface 31 is adapted to have a geometry that compliments the second inner surface 24 and comprises a third outer load-bearing surface 32 and a third outer non-load-bearing surface 33 which correspond with the second inner load-bearing surface 25 and the second inner non-load-bearing surface 26 respectively.

The third inner surface 34 comprises a third inner load-bearing surface 35 and a third inner non-load-bearing surface 36. The shape of the third inner surface 34 is formed of a partial cylindrical surface with rounded edges and comprising two opposed flat surfaces. The partial cylindrical surface and rounded edges act as the third inner load-bearing surface 35. The flat surfaces act as the third inner non-load-bearing surface 36.

Also shown relative to the third component 30 is the second axis 62 and a third axis 63 which is perpendicular to both the first axis 61 and the second axis 62. Thus all axes are orthogonal in relation to one another.

The second inner surface 24 and the third outer surface 31 are configured such that, when engaged with one another, the third component 30 is rotatable relative to the second component 20 about the second axis 62 only. In use, the second axis 62 aligns with an anatomical degree of freedom and provides medial and lateral rotation of a leg relative to a pelvis. Hence, the second axis 62 may be considered as the medial-lateral rotation axis in this embodiment of the invention.

Figure 5:
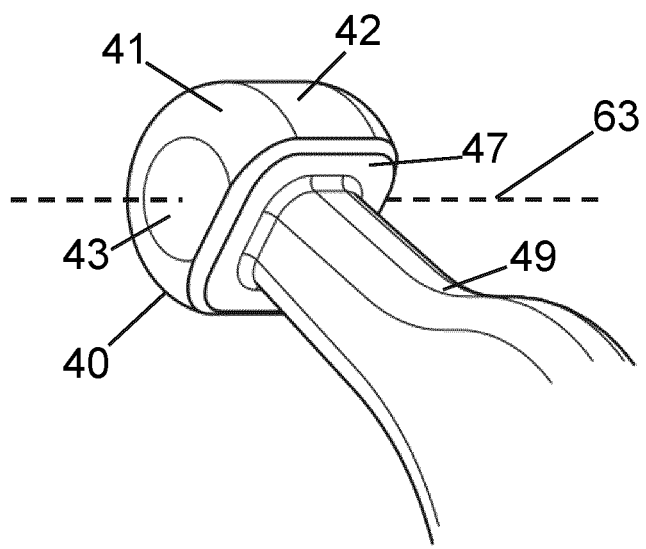
FIG. 5 is an illustration of the fourth component shown in FIG. 1.

Referring now to FIG. 5, the fourth component 40 is shown. The fourth outer surface 41 is adapted to have a geometry that compliments the third inner surface 34 and comprises a fourth outer load-bearing surface 42 and a fourth outer non-load-bearing surface 43 which correspond with the third inner load-bearing surface 35 and the third inner non-load-bearing surface 36 respectively.

Also shown relative to the fourth component 40 is the third axis 63.

The third inner surface 34 and the fourth outer surface 41 are configured such that, when engaged with one another, the fourth component 40 is rotatable relative to the third component 30 about the third axis 63. In use, the third axis 63 aligns with an anatomical degree of freedom and provides abduction and adduction of a leg relative to a pelvis. Hence, the third axis 63 may be considered as the abduction-adduction axis in this embodiment of the invention.

Figure 12:
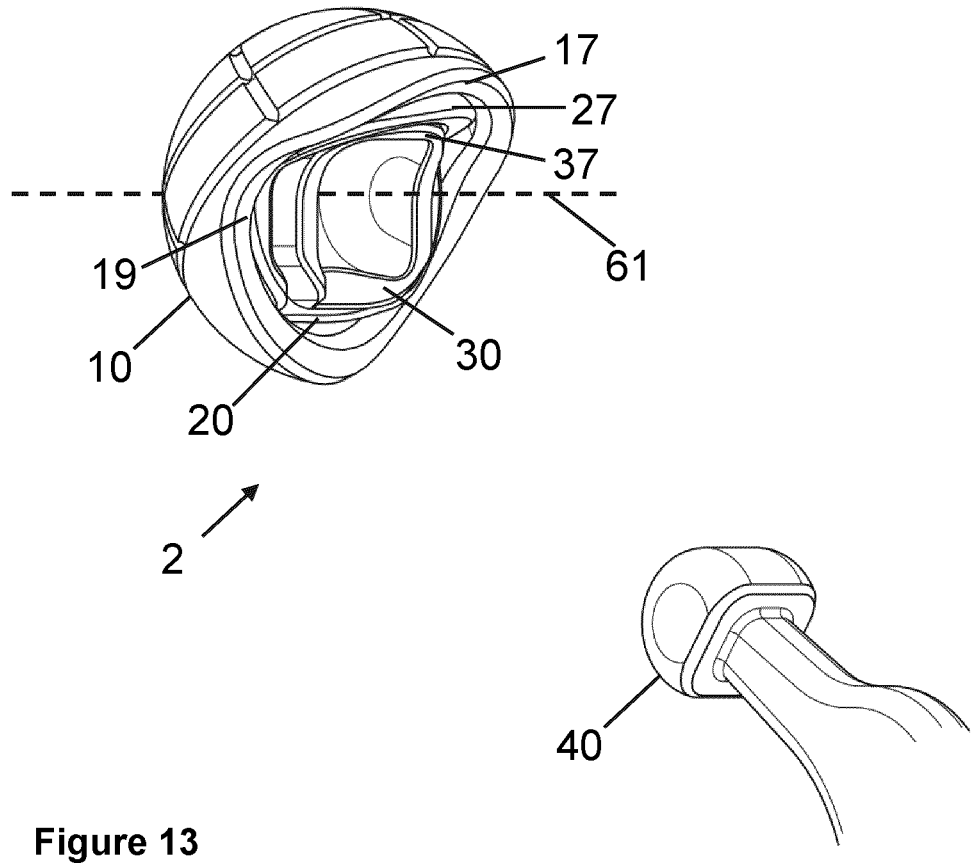
FIG. 12 is a further illustration of the prosthetic implant shown in FIGS. 1 and 6 to 11, here showing the second component engaged with the first component and rotated to the orientation it has in FIG. 8.
Figure 13:
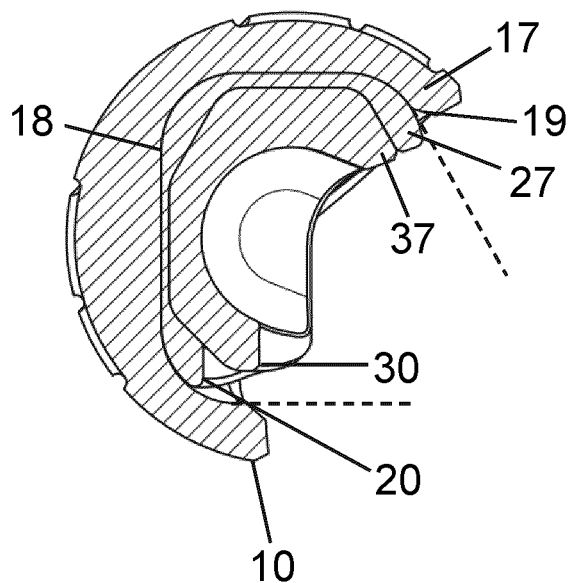
FIG. 13 is a cross-sectional illustration of the prosthetic implant shown in FIGS. 1 and 6 to 12, here showing the second component interlocked with the first component.
Figure 14:
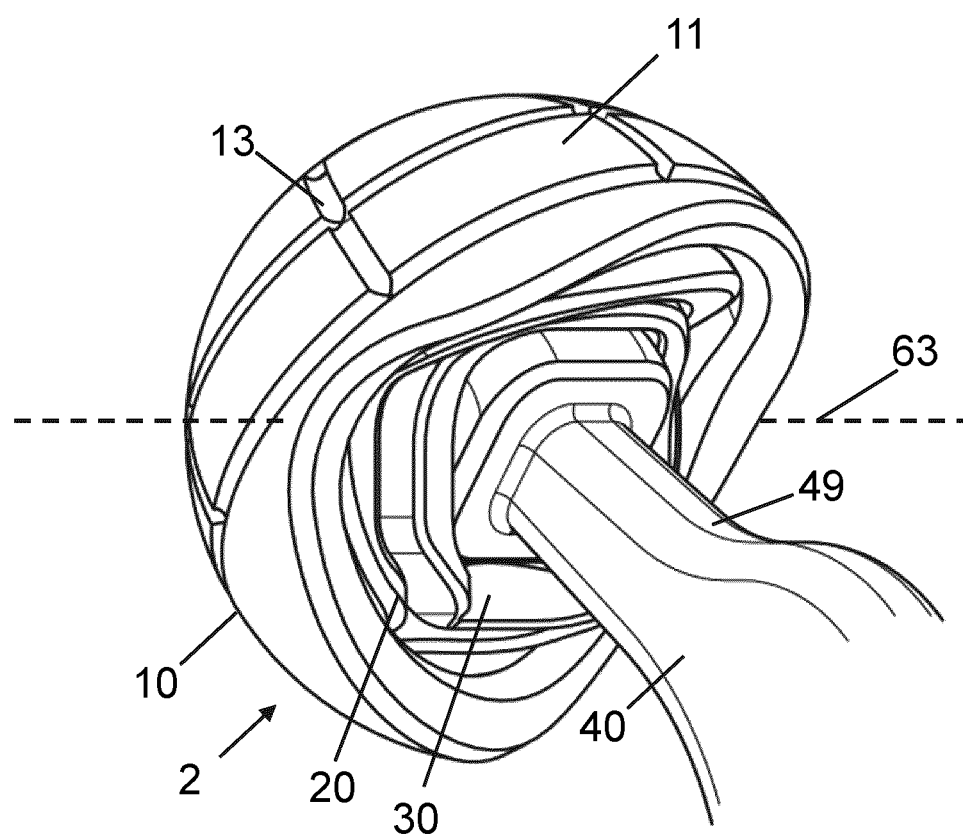
FIG. 14 is an illustration of the prosthetic implant shown in FIGS. 1 and 6 to 13, here showing the first, second, third and fourth components engaged with one another.

FIGS. 6 to 14 show the steps of assembling the four components 10, 20, 30, 40 shown in FIGS. 1 and 2, with the fully assembled form of the prosthetic implant 2 shown in FIG. 14.

Figure 6:
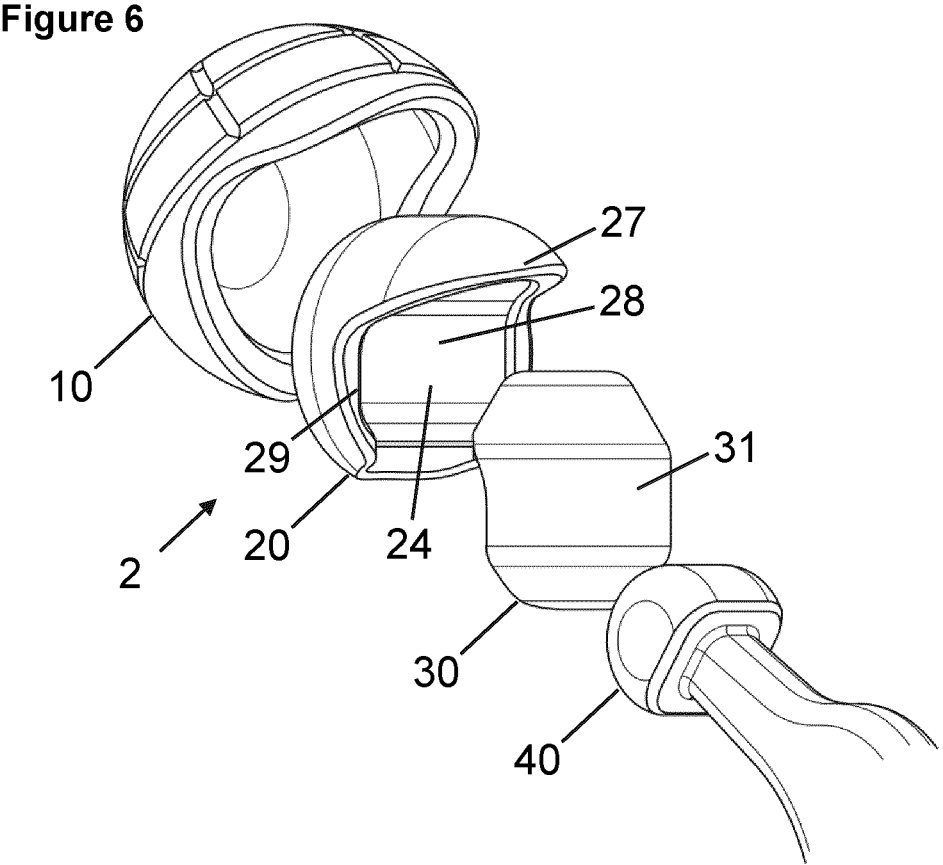
FIG. 6 is an illustration of the prosthetic implant shown in FIG. 1, here showing the third component rotated through 180°.

Referring now to FIG. 6, in order to assemble the prosthetic implant 2 and in particular to engage the third outer surface 31 with the second inner surface 24, the third component 30 may be rotated into the orientation shown in FIG. 6, by rotating it through 180° from the orientation shown in FIG. 1 (and relative to the other components 10, 20, 40).

Figure 7:
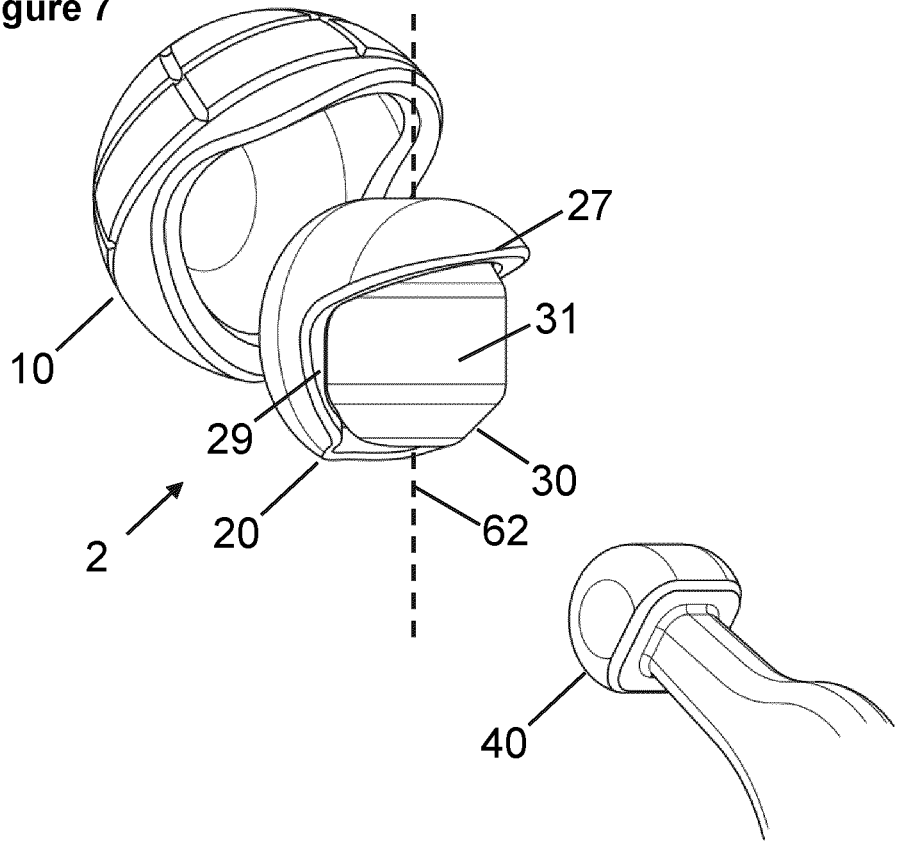
FIG. 7 is a further illustration of the prosthetic implant shown in FIGS. 1 and 6, here showing the third component engaged with the second component.

Referring now to FIG. 7, in order to engage the third outer surface 31 with the second inner surface 24, the third component 30 may be repositioned into the position shown in FIG. 7 by passing it through the second opening 29 and positioning it within the second recess 28. The third component 30 may thereby be brought in contact with the second component 20 such that it can rotate about the second axis 62.

Figure 8:
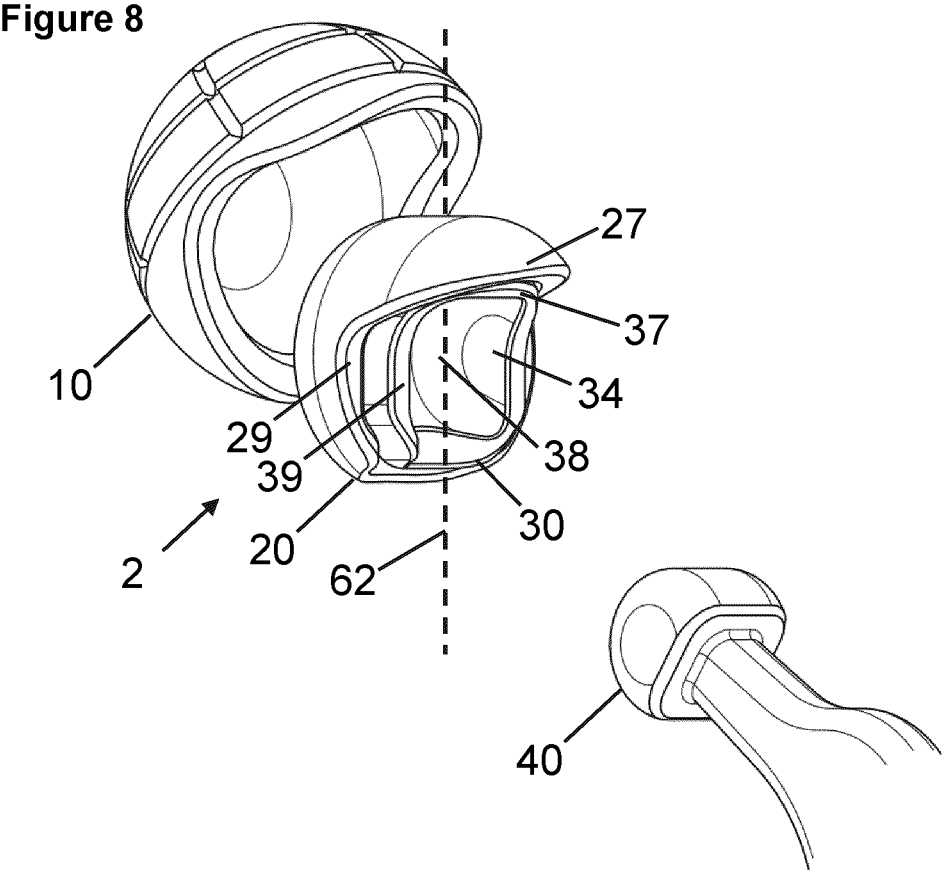
FIG. 8 is a further illustration of the prosthetic implant shown in FIGS. 1, 6 and 7, here showing the third component engaged with the second component and rotated to the orientation it has in FIG. 1.

Referring now to FIG. 8, in order to engage the third outer surface (31 in FIG. 7) with the second inner surface 24, the third component 30 may be rotated into the orientation shown in FIG. 8, by rotating it through 180° from the orientation shown in FIG. 7, about the second axis 62 (and relative to the other components 10, 20, 40).

The third outer surface 31 may thereby be engaged with the second inner surface 24 and further, the third outer surface 31 may be engaged with the second lip 27 such that the third component 30 is held within the second recess 28 and restricted by the second opening 29.

Figure 9:
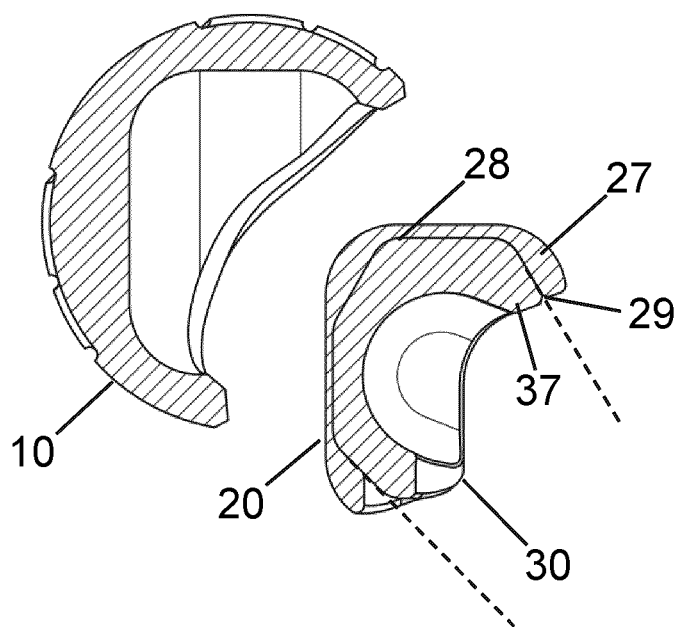
FIG. 9 is a further cross-sectional illustration of the prosthetic implant shown in FIGS. 1 and 6 to 8, here showing the third component interlocked with the second component.

The above interaction between the second component 20 and third component 30 is detailed further in FIG. 9 which provides a cross-sectional view of the first, second and third components 10, 20, 30. The second lip 27 is shown in line with the third lip 37 such that the two outermost planes of engagement between the second inner surface 24 and the third outer surface 31 form converging lines. The fact that these lines converge, prevents the third component 30 from sliding away from the second component 20.

In other words, the second lip 27 and third lip 37 are adapted such that maximal cross-sectional area of the third component 30 is larger than the area of the second opening 29. Hence, the third component 30 may be held within the second recess 28 such that the third component 30 remains in contact with the second component 20.

Figure 10:
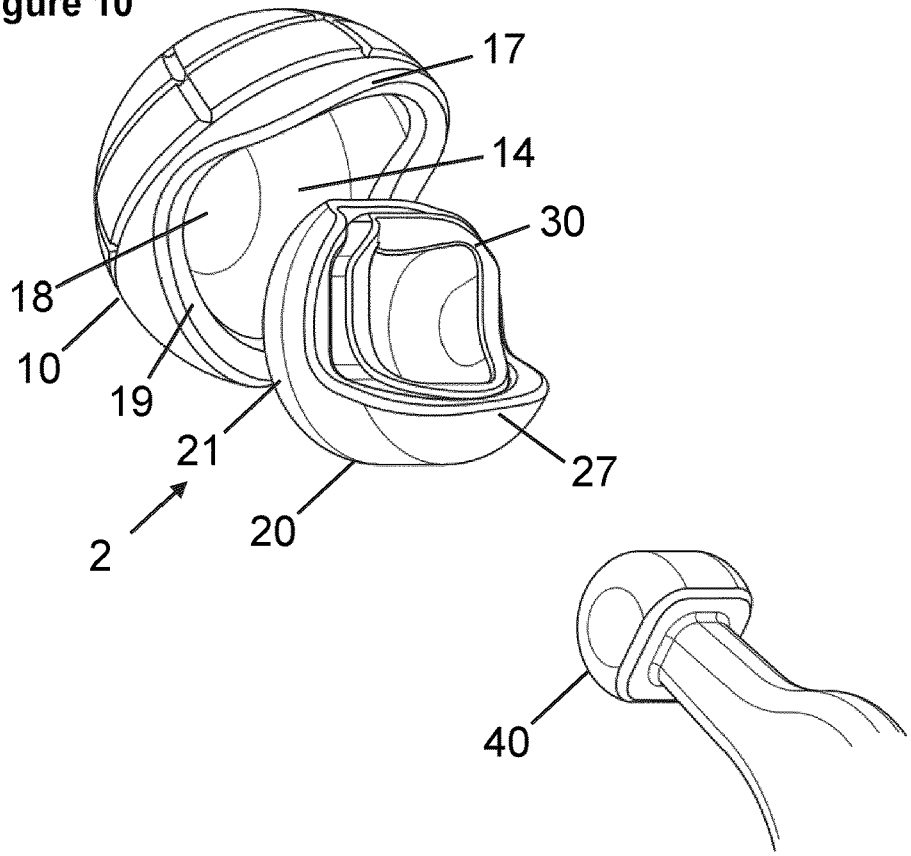
FIG. 10 is an illustration of the prosthetic implant shown in FIGS. 1 and 6 to 9, here showing the second and third components rotated through 180°.

Referring now to FIG. 10, in order to assemble the prosthetic implant 2 and in particular to engage the second outer surface 21 with the first inner surface 14, the second component 20 (with the third component 30 engaged within it) may be rotated into the orientation shown in FIG. 10, by rotating it through 180° from the orientation shown in FIG. 8 (and relative to the other components 10, 40).

Figure 11:
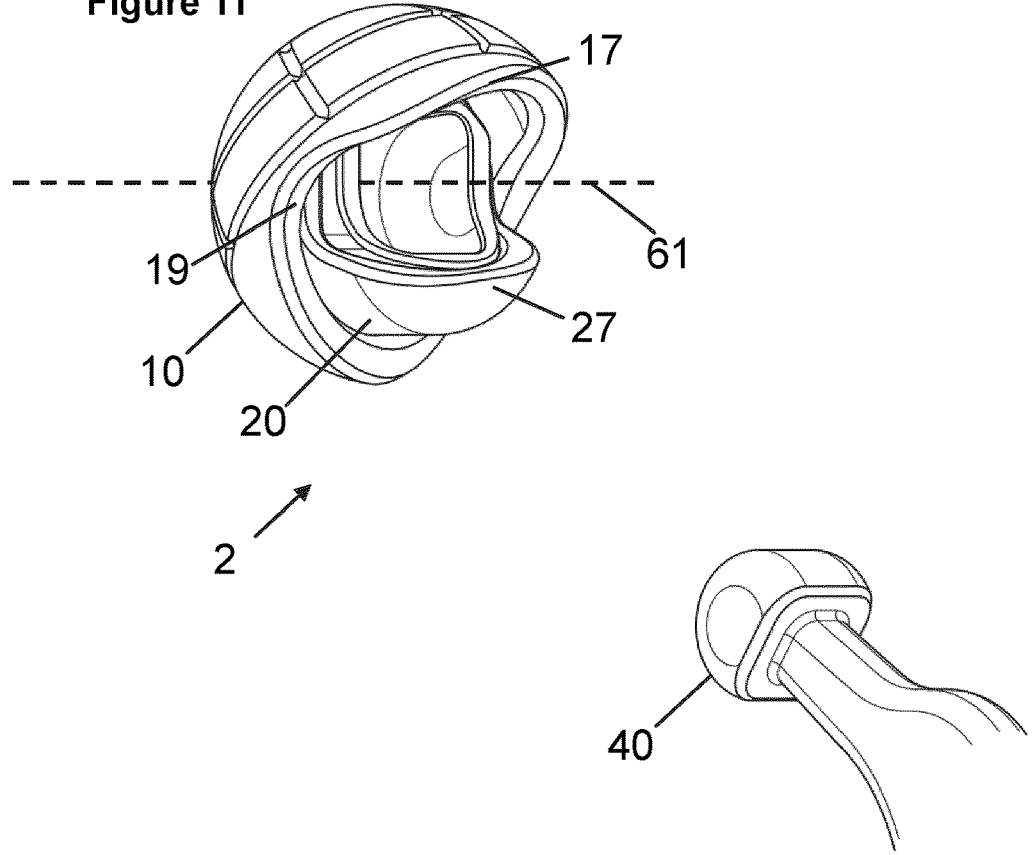
FIG. 11 is a further illustration of the prosthetic implant shown in FIGS. 1 and 6 to 10, here showing the second component engaged with the first component.

Referring now to FIG. 11, further in order to engage the second outer surface 21 with the first inner surface 14, the second component 20 (with the third component 30 engaged within the second recess 28) may be repositioned into the position shown in FIG. 11 by passing it through the first opening 19 and positioning it within the first recess 18. The second component 20 may thereby be brought in contact with the first component 10 such that it can rotate about the first axis 61.

Referring now to FIG. 12, in order to engage the second outer surface 21 with the first inner surface 14, the second component 20 (with the third component 30 engaged within the second recess 28) may be rotated into the orientation shown in FIG. 12, by rotating it through 180° from the orientation shown in FIG. 11, about the first axis 61 (and relative to the other components 10, 40).

The second outer surface 21 may thereby be engaged with the first inner surface 14 and further, the second outer surface 21 may be engaged with the first lip 17 such that the second component 20 is held within the first recess 18 and restricted by the first opening 19.

The above interaction between the first component 10 and second component 20 is detailed further in FIG. 13 which provides a cross-sectional view of the first, second and third components 10, 20, 30. The first lip 17 is shown in line with the second lip 27 such that the two outermost planes of engagement between the first inner surface 14 and the second outer surface 21 form converging lines. The fact that these lines converge, prevents the second component 20 from sliding away from the first component 10.

In other words, the first lip 17 and second lip 27 are adapted such that maximal cross-sectional area of the second component 20 is larger than the area of the first opening 19. Hence, the second component 20 may be held within the first recess 18 such that the second component 20 remains in contact with the first component 10.

Referring now to FIG. 13, a cross-sectional view of the first, second and third components 10, 20, 30 is shown. The interaction between the first and second components 10, 20 is similar to the respective interaction between the second and third components 20, 30 described in reference to FIG. 9. Accordingly, the first lip 17 is shown in line with the second lip 27 such that the two outermost planes of engagement between the first inner surface 14 and the second outer surface 21 form converging lines. The fact that these lines converge stops the second component 20 from sliding away from the first component 10.

The first lip and second lip are thereby adapted such that the maximal cross-sectional area of the second component 20 is larger than the area of the first opening 19. Hence, the second component may be held within the first recess 18 such that the second component remains in contact with the first component.

Referring now to FIG. 14, in order to assemble the prosthetic implant 2 and in particular to engage the fourth outer surface 41 with the third inner surface 34, the fourth component 40 may be repositioned such that the fourth outer surface 41 contacts the third inner surface 34. Further, the fourth outer surface 41 may contact and engage with the third inner surface 34 such that the fourth component 40 may rotate against the third component 30 and about the third axis 63.

Hence, each of the four components 10, 20, 30, 40 may be engaged with one another, following the steps set out above, to provide an assembled prosthetic implant 2 as shown in FIG. 14. The first outer surface 11 and the stem 49 are available to engage with the acetabulum and femur of a patient respectively.

Once the prosthetic implant 2 is assembled, it may be positioned within a patient as a step within total hip replacement surgery. The first outer surface 11 may be engaged with the acetabulum of the patient. The engagement feature 13 may aid in engagement of the first outer surface 11 with the acetabulum by permitting the first outer surface 11 to grip the surface of the pelvic bone and/or provide a more suitable surface for interaction with attachment means such as bone cement or bone growth-inducing material.

The stem 49 may similarly be engaged with the patient's femur, and as such the natural hip joint of the patient may be replaced with the prosthetic implant 2.

Once the prosthetic implant 2 is positioned within the patient, the first, second and third axes 61, 62, 63 correspond to the axes of revolution permitted by the natural hip joint. This alignment of the first, second and third axes to provide the natural degrees of freedom of the hip joint (flexion/extension, medial/lateral rotation and abduction/adduction) minimises the distance that the components 10, 20, 30, 40 slide past one another in use to achieve the desired rotation of the joint and resultant movement of the leg within the natural range of human movement. The reason that the overall sliding distance is reduced is that movements of the hip most commonly required of the prosthetic implant 2, when in use, will correspond closely with the first, second and third axes 61, 62, 63. Hence, a common movement of the prosthetic implant 2, in use, to travel from position A to position B may mainly require rotation about the first axis 61, whereas for a known prosthetic implant with separated axes of rotation, which is not aligned with the anatomical degrees of freedom, rotation about all three of its axes may be required to travel from position A to position B. The prosthetic implant 2 according to embodiments of the invention would therefore require a reduced overall sliding distance in comparison to known 'unaligned' prosthetic implants with separated axes of rotation. By minimising the sliding distance exhibited by the components 10, 20, 30, 40, the wear experienced by the prosthetic implant 2, in use, is in turn minimised also.

Further, alignment of the first, second and third axes 61, 62, 63 with the anatomical degrees of freedom results in loads that are transmitted through the prosthetic implant 2, when in use, acting normal to substantial regions of the load-bearing surfaces 15, 22, 25, 32, 35, 42. Hence the contact pressures, caused by loads transferred through the prosthetic implant 2 in use, are reduced and the resulting wear is also reduced.

Once the first outer surface 11 is engaged with the patient's acetabulum and the stem 49 is engaged with the patient's femur following a completed total hip replacement surgery, the patient's musculature surrounding the hip joint holds the fourth outer surface 41 in engagement with the third inner surface 34. If the fourth component 40 is engaged with the third component 30, the stem 49 makes it impossible for the third component 30 to rotate to an orientation at which it can pass through the second opening 29, and for the second component 20 to rotate to an orientation at which it can pass through the first opening 19. As such, the components 10, 20, 30, 40 are very unlikely to dislocate and cause the prosthetic implant 2 to fail.

Figure 15:
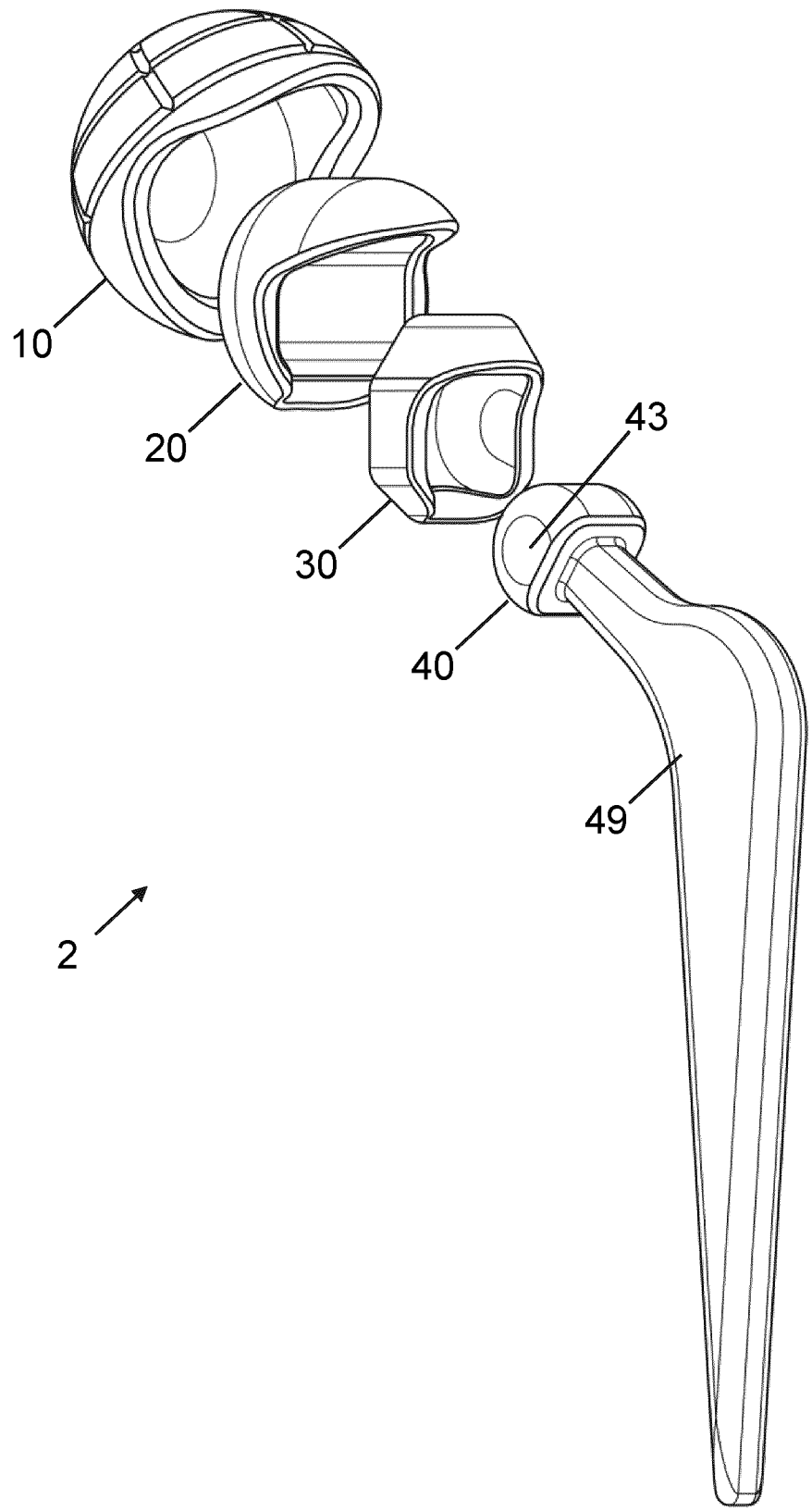
FIG. 15 is an exploded view of the prosthetic implant shown in FIGS. 1 and 6 to 14, here showing the first, second, third and fourth components including a stem extending from the fourth component.

Referring now to FIG. 15, the prosthetic implant 2 is shown with a full view of the fourth component 40 and the stem 49 that extends from it. The stem is integrally formed as part of the fourth component in a monobloc design. The flat fourth outer non-load-bearing surfaces 43 are parallel with flat surfaces on the stem 49, this makes the monobloc embodiment of the fourth component 40 simple to produce.

Figure 16:
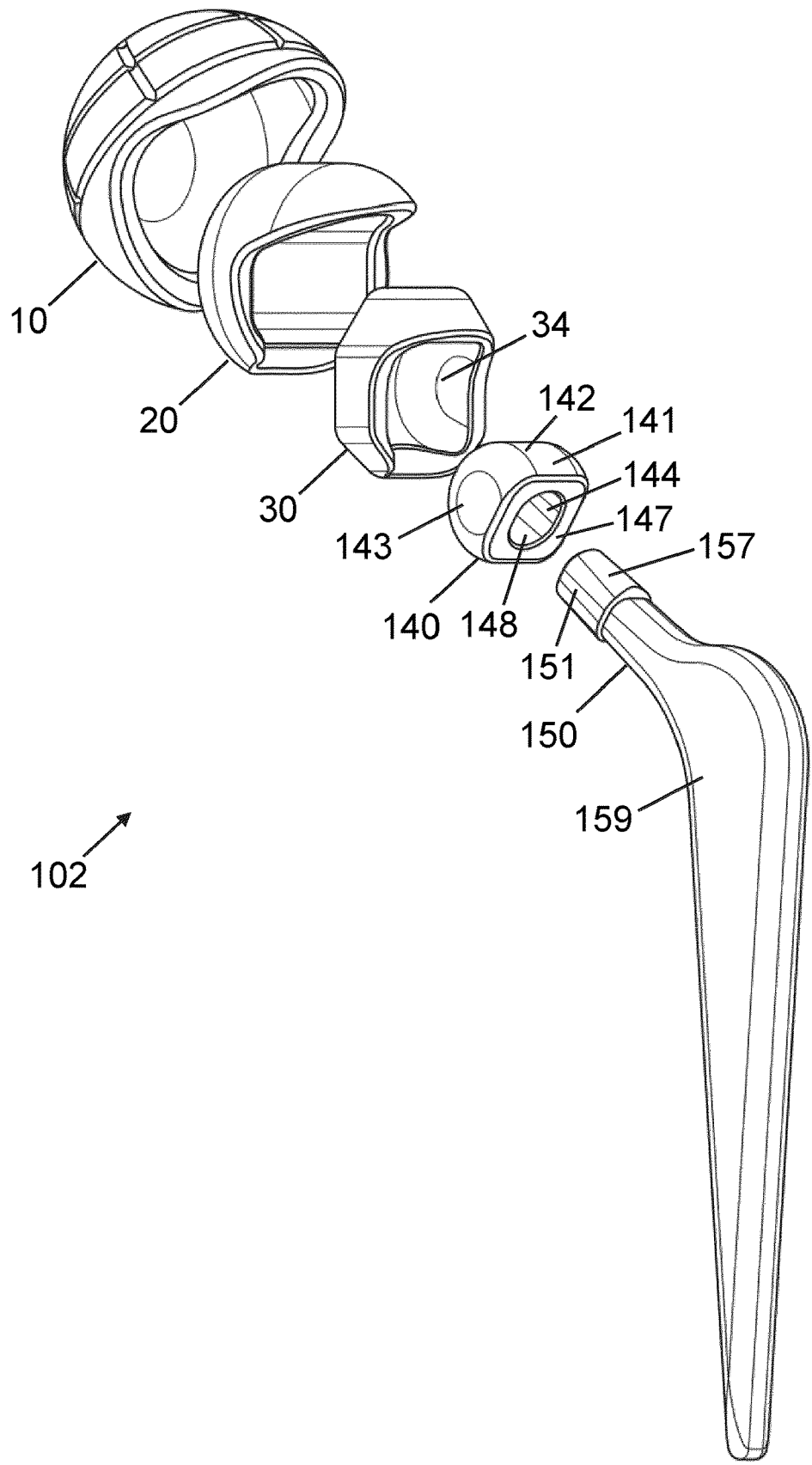
FIG. 16 is an exploded view of a prosthetic implant, according to a further embodiment of the first aspect of the present invention, showing first, second, third, fourth and fifth components spaced apart from one another.

Referring now to FIG. 16, a prosthetic implant according to a different embodiment of the first aspect of the present invention, is defined generally by the reference numeral 102. The prosthetic implant 102 comprises a first component 10, a second component 20, a third component 30, a fourth component 140, and a fifth component 150. The fourth component 140 comprises a head 147 and an outer surface 141 formed around the head 147 and adapted to contact and engage with the third inner surface 34 such that the fourth component 140 may rotate against the third component 30 and about the third axis 63. The fourth component further comprises a fourth recess 148 comprising at least one flat inner surface 144.

The fifth component 150 comprises a tapered protrusion 157 adapted to engage with the fourth recess 148 wherein the tapered protrusion comprises at least one flat outer surface 151 configured to engage with the at least one flat inner surface 144. The fifth component further comprises a stem 159 extending from the protrusion 157 and adapted to engage with the femur of a patient. The prosthetic implant 102 is thereby provided with a modular stem rather than the monobloc stem of prosthetic implant 2.

Figure 17:
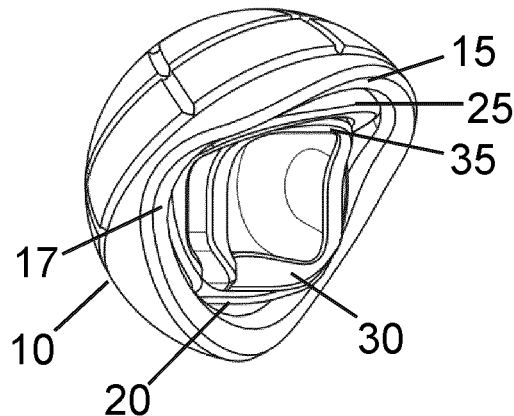
FIG. 17 is an illustration of the prosthetic implant shown in FIG. 16, here showing the first, second and third components engaged with one another.
Figure 17:
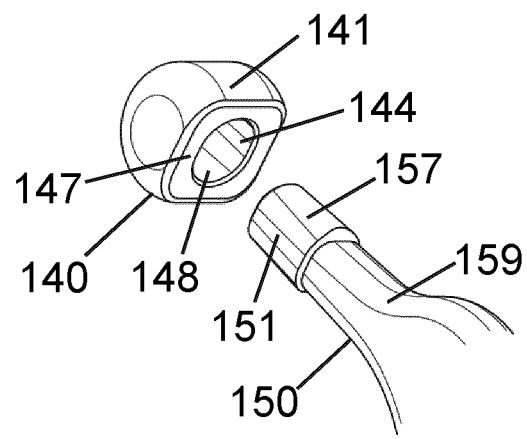
Figure 18:
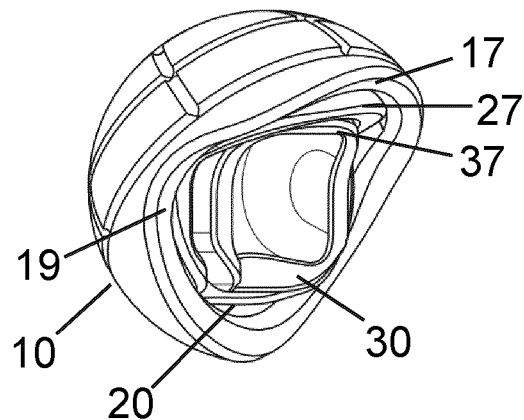
FIG. 18 is an illustration of the prosthetic implant shown in FIG. 17, here showing the fourth and fifth components engaged with one another.
Figure 18:
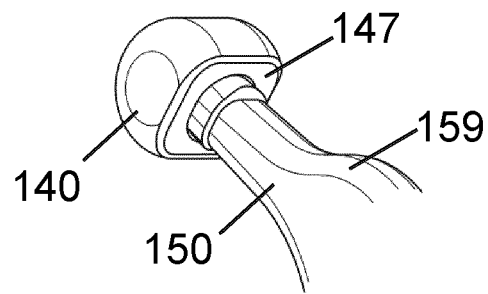

To assemble the modular stem embodiment of the invention relating to the prosthetic implant 102, there is an additional method step involved before engaging the fourth component 140 with the third component 30. FIGS. 17 and 18 show the steps of assembling the fourth component 140 and fifth component 150.

Referring now to FIG. 17, the first, second and third components 10, 20 and 30 are shown engaged with one another similarly to that shown in FIG. 12 for the monobloc stem embodiment relating to prosthetic implant 2. The fifth component 150 is shown with the tapered protrusion 157 aligned with the fourth recess 148 such that the at least one flat outer surface 151 is positioned to engage with the at least one flat inner surface 144.

Referring now to FIG. 18, the tapered protrusion 157 is engaged with the fourth recess 148, wherein at least one flat outer surface 151 provides alignment and prevents revolution as it is engaged with the at least one flat inner surface 144. Thereby, the fifth component 150 is engaged with the fourth component 140.

The assembly of the prosthetic implant 102 may, from there on, be completed in accordance with the method steps outlined for the assembly of prosthetic implant 2, with reference to FIG. 14.

Figure 19:
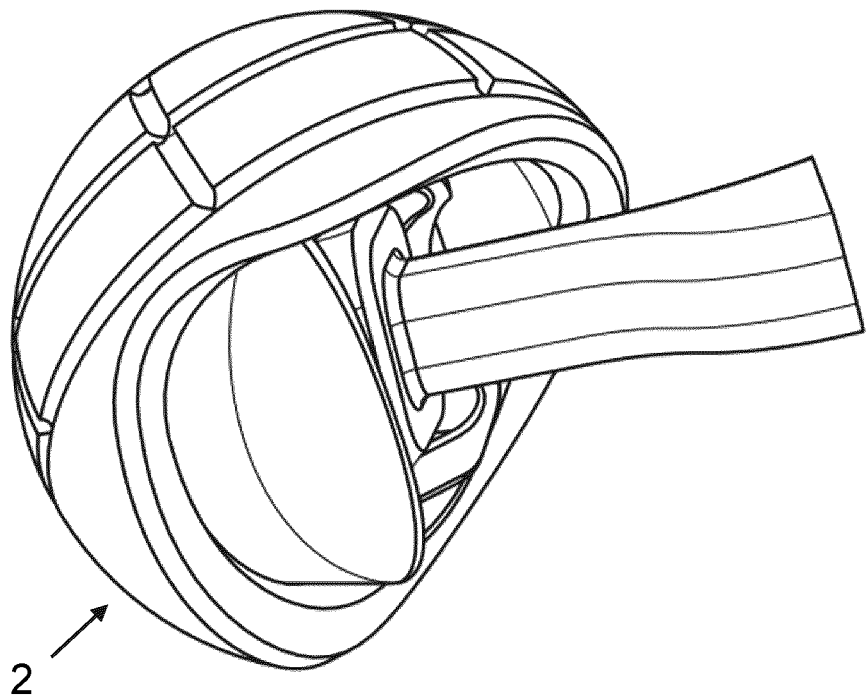
FIG. 19 is an illustration of the prosthetic implant shown in FIG. 14, shown here with a flexion of 110 degrees applied.
Figure 20:
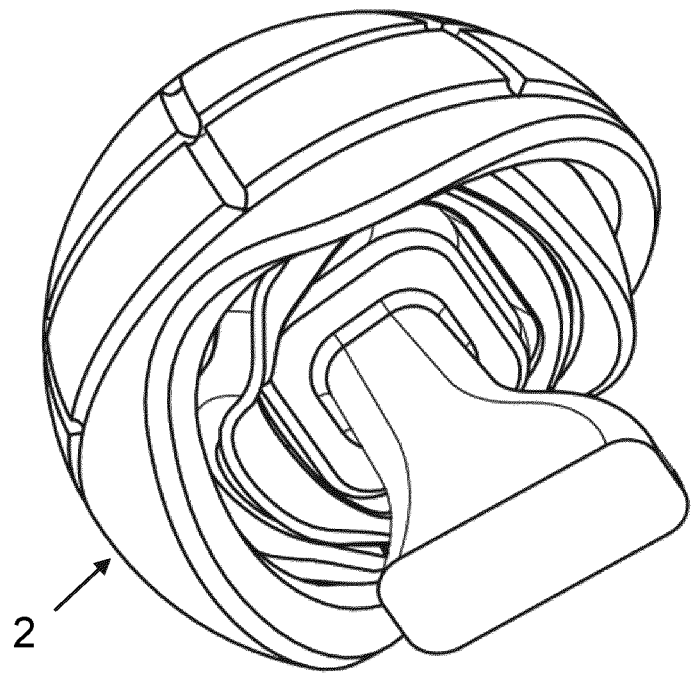
FIG. 20 is an illustration of the prosthetic implant shown in FIG. 14, shown here with an extension of 30 degrees applied.
Figure 21:
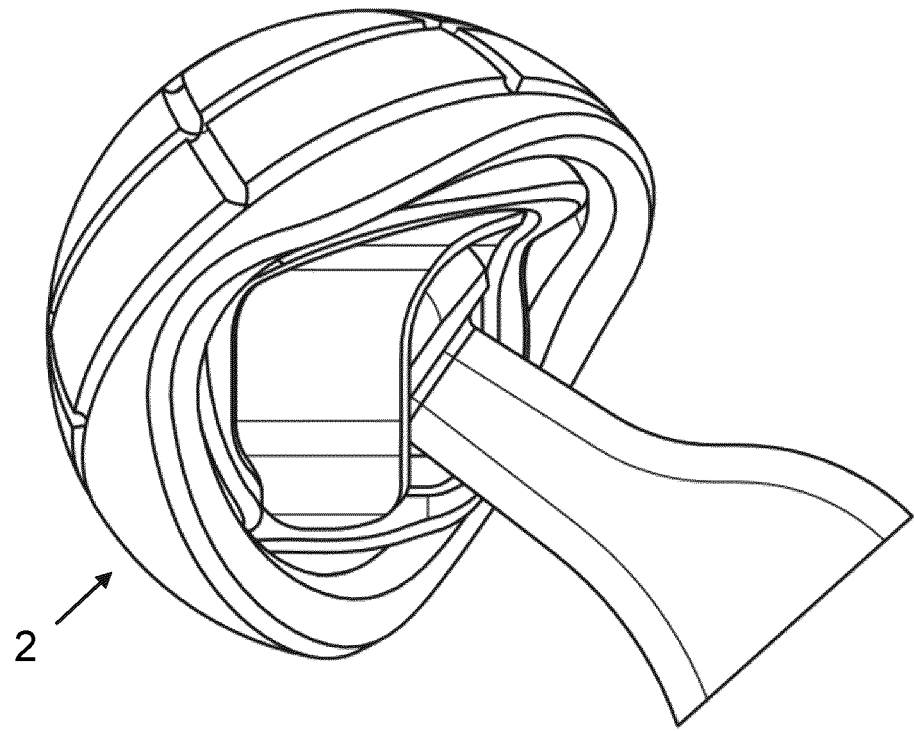
FIG. 21 is an illustration of the prosthetic implant shown in FIG. 14, shown here with a medial rotation of 45 degrees applied.
Figure 22:
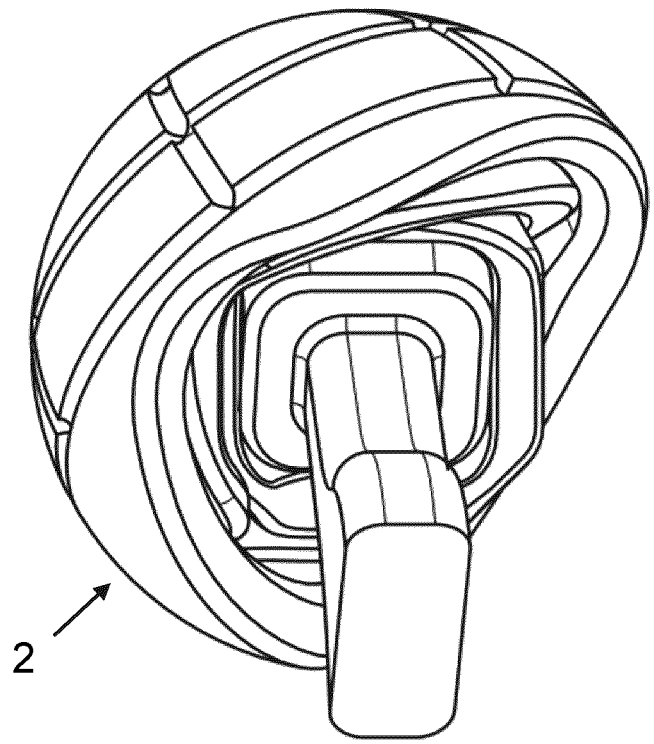
FIG. 22 is an illustration of the prosthetic implant shown in FIG. 14, shown here with a lateral rotation of 45 degrees applied.
Figure 23:
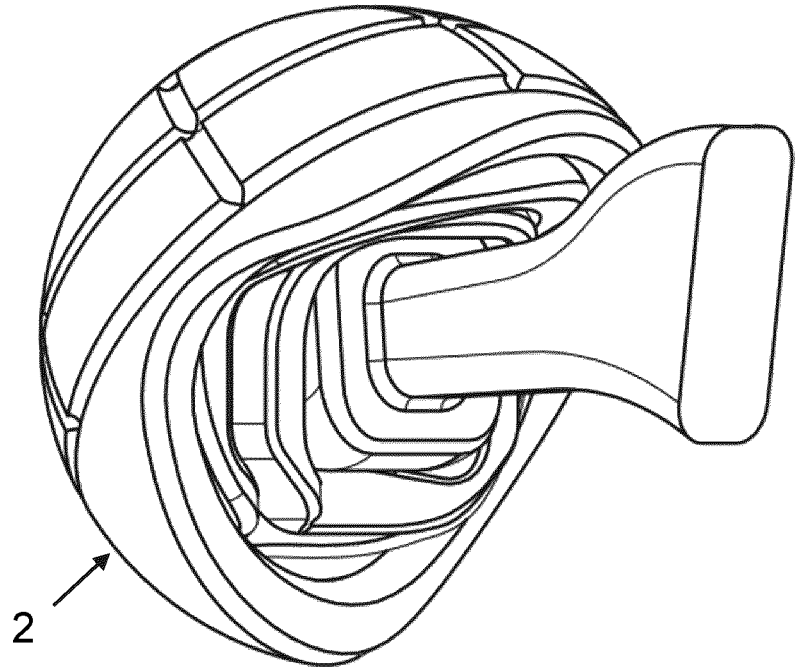
FIG. 23 is an illustration of the prosthetic implant shown in FIG. 14, shown here with an abduction of 40 degrees applied.
Figure 24:
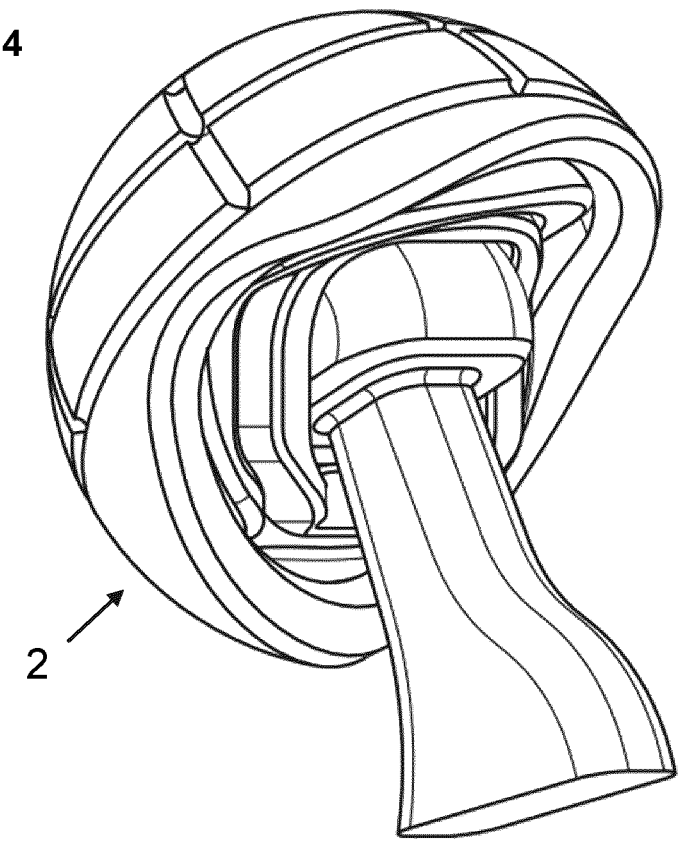
FIG. 24 is an illustration of the prosthetic implant shown in FIG. 14, shown here with an adduction of 30 degrees applied.

Referring now to FIGS. 19 to 24, an assembled prosthetic implant 2, as shown in FIG. 14, is shown in a variety of different positions following the rotation of one component relative to another. FIG. 19 shows the prosthetic implant 2 having experienced 110 degrees of flexion from the position that is shown in FIG. 14. FIGS. 20 to 24 show the prosthetic implant 2 having similarly experienced varying degrees of extension, medial rotation, lateral rotation, abduction and adduction respectively, each having started from the position shown in FIG. 14. Overall, FIGS. 19 to 24 show the wide range of movement that is possible for the prosthetic implant 2 without any components impinging on one another or dislocating from one another.

Referring now to FIGS. 25 and 26, the results of a standard test to measure the wear of total hip-joint prostheses (ISO 14242-1) are presented. In FIG. 25, the wear rate of a known ball-and-socket type prosthetic implant that uses UHMWPE as the soft bearing is compared to the wear rate of an embodiment of the invention in which the first and third components are formed of UHMWPE whereas the second and fourth components are formed of high-nitrogen austenitic stainless steel.

The wear rate of the ball and socket prosthesis resulted to be 29.1 (mg/million cycles) whereas the wear rate of the embodiment resulted to be 7.1 (mg/million cycles). The wear rate of the embodiment of the invention was therefore less than a quarter of that of known ball and socket prosthesis.

In FIG. 26, the wear rate of a known ball-and-socket type prosthetic implant that uses crosslinked polyethylene (XPE) as the soft bearing is compared to the wear rate of an embodiment of the invention in which the first and third components are formed of XPE whereas the second and fourth components are formed of high-nitrogen austenitic stainless steel. The wear rate of the ball and socket prosthesis resulted to be 4.5 (mg/million cycles) whereas the wear rate of the embodiment of the invention resulted to be −1.0 (mg/million cycles). The negative wear rate represents fluid uptake of the XPE (even after being corrected by fluid absorption data using the loaded soak control). This implies a significantly lower wear rate of the prosthesis of the invention as compared to the ball and socket design.

UHMWPE and XPE were selected as the soft bearing materials for the tests since these represent the two main types of polymers which are used in the field.

This significant reduction in wear will correspond to prosthetic implants according to embodiments of the invention lasting significantly longer than known prosthetic implants currently existing in the field. Therefore, current requirements to replace prosthetic implants every few years, with substantial surgeries that require lengthy recovery times, would be greatly improved upon with use of prosthetic implants according to embodiments of the invention.

The invention claimed is:

1. A prosthetic implant comprising:
a first component comprising a first inner surface and a first outer surface,
a second component comprising a second outer surface adapted to contact and engage with the first inner surface, the second component further comprising a second inner surface,
a third component comprising a third outer surface adapted to contact and engage with the second inner surface, the third component further comprising a third inner surface, and
a fourth component comprising a fourth outer surface adapted to contact and engage with the third inner surface;
wherein the second component is rotatable relative to the first component about a first axis, the third component is rotatable relative to the second component about a second axis perpendicular to the first axis, and the fourth component is rotatable relative to the third component about a third axis perpendicular to the first axis and second axis;
the first inner surface and the second outer surface are each formed with a first partial cylindrical shape, the first inner surface and the second outer surface each comprise a flat surface normal to the first axis and are engageable with one another such that the second component is rotatable relative to the first component about the first axis only,
the second inner surface and the third outer surface are each formed with a second partial cylindrical shape, the second inner surface and the third outer surface each comprise a flat surface normal to the second axis and are engageable with one another such that the third component is rotatable relative to the second component about the second axis only, and
the third inner surface and the fourth outer surface are each formed with a third partial cylindrical shape, the third inner surface and the fourth outer surface each comprise a flat surface normal to the third axis and are engageable with one another such that the fourth component is rotatable relative to the third component about the third axis only.

2. A prosthetic implant according to claim 1, wherein the first, second and third inner surfaces and the second, third and fourth outer surfaces are each continuous.

3. A prosthetic implant according to either claim 1, wherein one or more of the first, second and third partial cylindrical shapes comprises a flat surface and a unilaterally curved surface.

4. A prosthetic implant according to claim 3 wherein at least one of: the flat surface and the unilaterally curved surface is adapted to act as the primary load-bearing surface when the prosthetic implant is in use.

5. A prosthetic implant according to either claim 1, wherein one or more of the first, second and third partial cylindrical shapes comprises a flat surface, a unilaterally curved surface and a truncated conical surface.

6. A prosthetic implant according to claim 5 wherein at least one of: the flat surface, the unilaterally curved surface and the truncated conical surface is adapted to act as the primary load-bearing surface when the prosthetic implant is in use.

7. A prosthetic implant according to claim 1, wherein the partial cylindrical shape comprises a rounded corner.

8. A prosthetic implant according to claim 1, wherein the first inner surface forms a first recess comprising a first opening; the first component further comprises a first lip adapted to define part of the opening and shaped such that the area of the first opening is smaller than the maximal cross-sectional area of the first recess; and the second component is engageable with the first component such that the second component is held within the first recess.

9. A prosthetic implant according to claim 8, wherein the second component is further engageable with the first lip such that the second component is held within the first recess.

10. A prosthetic implant according to either claim 8, wherein the second inner surface forms a second recess comprising a second opening; the second component further comprises a second lip adapted to define part of the opening and shaped such that the area of the second opening is smaller than the maximal cross-sectional area of the second recess; and the third component is engageable with the second component such that the third component is held within the second recess.

11. A prosthetic implant according to claim 10, wherein the third component is further engageable with the second lip such that the third component is held within the second recess.

12. A prosthetic implant according to claim 1, wherein the first outer surface is adapted such that, in use, it is engageable with an acetabulum.

13. A prosthetic implant according to claim 1, wherein the first outer surface further comprises an engagement feature adapted such that, in use, the first component is engageable with an acetabulum.

14. A prosthetic implant according to claim 1, wherein the fourth component further comprises a stem, which stem is engageable, in use, with a femur.

15. A prosthetic implant according to claim 1, wherein the prosthetic implant further comprises a fifth component, engageable with the fourth component and comprising a stem, which stem is, in use, engageable with a femur.

16. A prosthetic implant according to claim 15, wherein the fifth component further comprises a tapered protrusion with at least one flat inner surface, and the fourth component further comprises a fourth recess that is tapered with at least one flat outer surface and configured complementarily to the tapered protrusion of the fifth component.

17. A prosthetic implant according to claim 1, wherein, in use, the first axis aligns with a flexion and extension axis defined by a natural hip joint.

18. A prosthetic implant according to claim 1, wherein, in use, the second axis aligns with a medial and lateral rotation axis defined by a natural hip joint.

19. A prosthetic implant according to claim 1, wherein, in use, the third axis aligns with an abduction and adduction axis defined by a natural hip joint.

20. A prosthetic implant according to claim 1, wherein each of the first, second and third inner surfaces and the second, third and fourth outer surfaces comprise a load-bearing surface or a non-load-bearing surface or both.

21. A prosthetic implant according to claim 1, wherein one or more of the first, second, third and fourth components is formed of ultra-high-molecular-weight polyethylene or crosslinked polyethylene.

22. A prosthetic implant according to claim 1, wherein the first, second, third and fourth components are formed of alternating polymeric and metallic materials, or alternating polymeric and ceramic materials, or any combination of polymeric, metallic and ceramic materials.

23. A method for assembling a prosthetic implant comprising a first component comprising a first outer surface and a first inner surface, a second component comprising a second outer surface and a second inner surface, a third component comprising a third outer surface and a third inner surface and a fourth component comprising a fourth outer surface, wherein the second component is rotatable relative to the first component about a first axis, the third component is rotatable relative to the second component about a second axis perpendicular to the first axis and the fourth component is rotatable relative to the third component about a third axis perpendicular to the first axis and second axis; the method comprising the steps:
    engaging the third component with the second component,
    rotating the third component relative to the second component, about the second axis, until the third outer surface becomes rotatably interlocked in contact with the second inner surface,
    engaging the second component with the first component,
    rotating the second component relative to the first component, about the first axis, until the second outer surface becomes rotatably interlocked with the first inner surface, and
    engaging the fourth component with the third component;
    wherein the first component further comprises a first recess comprising a first opening shaped to have a smaller opening area than the maximal cross-sectional area of the first recess; and the method step of engaging the second component with the first component comprises the steps of
        orienting the second component such that it can pass through the first opening,
        positioning the second component through the first opening into the first recess, and
        contacting and engaging the second outer surface with the first inner surface; and/or
    wherein the second component further comprises a second recess comprising a second opening shaped to have a smaller opening area than the maximal cross-sectional area of the second recess; and the method step of engaging the third component with the second component comprises the steps of
        orienting the third component such that it can pass through the second opening,
        positioning the third component through the second opening into the second recess, and
        contacting and engaging the third outer surface with the second inner surface.

24. A method of fitting a prosthetic implant comprising a first component comprising a first outer surface and a first inner surface, a second component comprising a second outer surface and a second inner surface, a third component comprising a third outer surface and a third inner surface and a fourth component comprising a fourth outer surface, wherein the second component is rotatable relative to the first component about a first axis, the third component is rotatable relative to the second component about a second axis perpendicular to the first axis; the method comprising the steps:
- engaging the third component with the second component,
- rotating the third component relative to the second component, about the second axis, until the third outer surface becomes rotatably interlocked in contact with the second inner surface,
- engaging the second component with the first component,
- rotating the second component relative to the first component, about the first axis, until the second outer surface becomes rotatably interlocked in contact with the first inner surface,
- fixing the first component to an acetabulum of a patient,
- fixing the fourth component to a femur of the patient, and
- engaging the fourth component with the third component;
- wherein the first component further comprises a first recess comprising a first opening shaped to have a smaller opening area than the maximal cross-sectional area of the first recess; and the method step of engaging the second component with the first component comprises the steps of:
  - orienting the second component such that it can pass through the first opening,
  - positioning the second component through the first opening into the first recess, and
  - contacting and engaging the second outer surface with the first inner surface; and/or
- wherein the second component further comprises a second recess comprising a second opening shaped to have a smaller opening area than the maximal cross-sectional area of the second recess; and the method step of engaging the third component with the second component comprises the steps of
  - orienting the third component such that it can pass through the second opening,
  - positioning the third component through the second opening into the second recess, and
  - contacting and engaging the third outer surface with the second inner surface.

* * * * *